(12) United States Patent
de Groot et al.

(10) Patent No.: US 6,924,412 B1
(45) Date of Patent: Aug. 2, 2005

(54) MEANS AND METHODS FOR RAISING ANTIBODY CONCENTRATION IN COMPARTMENTS OF THE BODY OF A NON-HUMAN ANIMAL

(75) Inventors: Nanda de Groot, Leiden (NL); Herman Albert de Boer, Roelofarendsveen (NL)

(73) Assignee: Arriwan Holding B.V., Roelfarendsveen (NL)

( * ) Notice: Subject to any disclaimer, the term of this patent is extended or adjusted under 35 U.S.C. 154(b) by 349 days.

(21) Appl. No.: 09/621,593

(22) Filed: Jul. 21, 2000

(51) Int. Cl.$^7$ ................................................ C12P 21/00
(52) U.S. Cl. ............................... 800/7; 800/4; 800/13; 800/14; 800/15; 800/18; 800/21; 800/25
(58) Field of Search ............................. 800/4, 7, 8, 13, 800/14, 18, 25, 15, 10, 24; 424/93.21, 93.2; 435/455; 514/44

(56) References Cited

U.S. PATENT DOCUMENTS 5,895,833 A * 4/1999 Berg ........................... 800/14
6,042,833 A * 3/2000 Mostov et al. ............ 424/193.1

OTHER PUBLICATIONS

Anderson, Human gene therapy, 1998, NATURE, vol. 392, pp. 25–30.*
De Groot et al., Over–extension of the murine polymeric immunoglobulin receptor gene in the mammary gland of transgenic mice, 1999, Transgenic Research, vol. 8, pp. 125–135.*
Moreadith et al., Gene targeting in embryonic stem cells: the new physiology and metabolsim, 1997, J. Mol. Med., vol. 75, pp. 208–216.*
Chiu et al, Optimizing energy potentials for success in protein tertiary structure prediction, 1998, Folding & Design, vol. 3, pp. 223–228.*
Ghetie et al., Multiple roles for the major histocompatibility complex class I–related receptor FcRn, 2000, Annual Review of Immunology, vol. 18, pp. 739–766.*
Kacskovics et al., Cloning and characterization of the Bovine MHC Class I–like Fc receptor, 2000, The Journal of Immunology, pp. 1890–1897.*
Strojek et al., The use of transgenic animal techniques for livestock improvement, 1988, Genetic Engineering: Principles and Methods, vol. 10, pp. 221–246.*
Wall, Transgenic Livestock: Progress and Prospects for the future, 1996, Theriogenology, vol. 45, pp. 57–68.*
Houdebine, Production of pharmaceutical proteins from transgenic animals, 1994, Journal of Biotechnology, vol. 34, pp. 269–287.*
Hammer et al., Genetic engineering of mammalian embryos, 1986, J. Anim. Sci., vol. 63, pp. 269–278.*
Mullins et al., Perspectives Series: Molecular medicine in genetically engineered animals, 1996, J. Clin. Invest., vol. 97, pp. 1557–1560.*
Ebert et al., A moloney MLV–Rat somatotropin fusion gene produces biologically active somatotropin in a transgenic pig, 1988, Molecular Endocrinology, pp. 277–283.*
Kappel et al., Regulating gene expression in transgenic animals, 1992, Current Opinion in Biotechnology, vol. 3, pp. 548–533.*
Ackermann et al., IL–4 and IFN–y increase steady state levels of polymeric Ig receptor mRNA in human airway and intestinal epithelial cells, 1999, The Journal of Immunology, pp. 5112–5118.*
Lamm, Current concepts in mucosal immunity IV. How epithelial transport of IgA antibodies relates to host defense, 1998, THEMES, pp. G614–G617.*
Kaetzel, Polymeric Ig receptor: Defender of the fort or trojan horse?, 2001, Current Biology, vol. 11, pp. R35–R38.*
Tan et al., Bovine alpha–sl–casein gene sequences direct expression of variant of human tissue plasminogen activator in the milk of transgenic mice, www.ncbi.nlm.nih.gov, printed Oct. 17, 2002. Abstract Only.
Kim et al., High–level expression of human lactoferrin in milk of transgenic mice using lactoferrin sequence, www.ncbi.nlm.nih.gov, printed Oct. 17, 2002. Abstract Only.
Bijvoet et al., Recombinant human acid alpha–glucosidase: high level production in mouse milk, biochemical characteristics, correction of enzyme deficiency in GSDII KO mice, Human Molecular Genetics, 1998, pp. 1815–1824, vol. 7, No. 11, Oxford University Press.
Yarus et al., Production of active bovine tracheal antimicrobial peptide in milk of transgenic mice, Proc. Natl. Acad. Sci., Nov. 1996, pp. 14118–14121, vol. 93.
Hyttinen et al., High–level expression of bovine beta–lactoglobulin gene in transgenic mice, Journal of Biotechnology, 1998, pp. 191–198, vol. 61.
Theuer et al., Angiotensin II induced inflammatio in the kidney and in the heart of double transgenic rats, www.pubmedcentral.nih.gov, printed Oct. 17, 2002. pp. 1–16.
Ju et al., Conditional and targeted overexpression of vascular chymase causes hypertension in transgenic mice, PNAS, Jun. 19, 2001, pp. 7469–7474, vol. 98, No. 13.

(Continued)

*Primary Examiner*—Scott D. Priebe
*Assistant Examiner*—Brian Whiteman
(74) *Attorney, Agent, or Firm*—TraskBritt

(57) ABSTRACT

Methods and processes for raising the concentration of a first class of immunoglobulin relative to at least a second class of immunoglobulin in a compartment of the body of a non-human animal or the progeny thereof, as well as the animals produced by such methods and processes. Such methods and processes provide for the collection of antibodies produced by mucosal surfaces of the animal. Preferably, the production is in the mammary gland. Antibodies can be collected from the milk of the animal. Antibodies may be used for medical and/or nutritional purposes.

10 Claims, 7 Drawing Sheets

OTHER PUBLICATIONS

Takahashi et al., The milk protein promoter is a useful tool for developing a rat with tolerance to a human protein, Transgenic Research, 2001, pp. 571–575, vol. 10, Kluwer Academic Publishers, The Netherlands.

Kulseth et al., Cloning aned characterization of two forms of bovine polymeric immunoglobulin receptor cDNA, www.ncbi.nlm.nih.gov, printed Oct. 17, 2002. Abstract Only.

Fujiwara et al., Analysis of control elements for position–independent expression of human alpha–lactalbumin YAC, www.ncbi.nlm.nih.gov, printed Oct. 17, 2002. Abstract Only.

Brink, et al., Developing Efficient Strategies for the Generation of Transgenic Cattle which Produce Biopharmaceuticals in milk, Theriogenology, 2000, pp. 139–148, vol. 53, Elsevier Science Inc.

Van Berkel et al., Large scale production of recombinant human lactoferrin in the milk of transgenic cows, www.nature.com, printed Jun. 26, 2002. pp. 484–487.

Hirabayaski et al., A comparative study on the integration of exogenous DNA into mouse, rat, rabbit and pig genomes, www.ncbi.nlm.nih.gov, printed Oct. 17, 2002. Abstract Only.

Hyttinen et al., High–level expression of bovine beta–lactoglobulin gene in transgenic mice, www.ncbi.nlm.nib.gov, printed Oct. 17, 2002. Abstract Only.

Gutierrez et al., Expression of a bovine kappa–CN cDNA in the mammary gland of transgenic mice utilizing a genomic milk protein gene as an expression cassette, www.ncbi.nlm.nib.gov, printed Oct. 17, 2002. Abstract Only.

Cerdan et al., Accurate spatial and temporal transgene expression driven by a 3.8–kilobase promoter of the bovine beta–casein gene in the lactating mouse mammary gland, www.ncbi.nlm.nih.gov, printed Oct. 17, 2002. Abstract Only.

* cited by examiner

A.

B.

SEQUENCE LISTING

```
<160> NUMBER OF SEQ ID NOS: 4

<210> SEQ ID NO 1
<211> LENGTH: 16
<212> TYPE: DNA
<213> ORGANISM: Artificial Sequence
<220> FEATURE:
<223> OTHER INFORMATION: PCR Primer

<400> SEQUENCE: 1
cttgggagag gaactg                                                  16

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2
agctacttcc ttctctccag g                                            21

<210> SEQ ID NO 3
<211> LENGTH: 21
<212> TYPE: DNA
<213> ORGANISM: Artificial Sequence
<220> FEATURE:
<223> OTHER INFORMATION: PCR primer
```

```
<400> SEQUENCE: 3
aagacagtta ccaagagcgt g                                         21

<210> SEQ ID NO 4
<211> LENGTH: 28
<212> TYPE: DNA
<213> ORGANISM: Artificial Sequence
<220> FEATURE:
<223> OTHER INFORMATION: Oligonucleotide probe

<400> SEQUENCE: 4
atcgatgggt tgatgatcaa ggtgatgg                                  28
```

MEANS AND METHODS FOR RAISING ANTIBODY CONCENTRATION IN COMPARTMENTS OF THE BODY OF A NON-HUMAN ANIMAL

TECHNICAL FIELD

The invention relates to the field of immunology and antibodies.

BACKGROUND

It has long since been recognized that antibodies play an important role in the protection against pathogens not only in the blood but also in fluids that are excreted into the mucosal surfaces of the body. Many pathogens invade the body via the mucosal surfaces. Such surfaces are inherently vulnerable to invasion and colonization by these organisms. Dimeric IgA (dIga) plays an important role in the immune protection of the mucosal and glandular surfaces by blocking entry of the antigens into the mucosal tissues and by neutralizing microbial pathogens (Kaetzel et al., 1991; Mazanec et al., 1992; Mazanec et al., 1993; Lamm, 1997). The pIgR transports polymeric immunoglobulins of the IgA and IgM class, produced by plasma cells within the interstitial space underlying the mucosae, across the epithelial cell layer of the mucosal and glandular surfaces (such as the gastrointestinal tract, respiratory tract, genital tract and mammary gland) into the external secretions (Childers et al., 1989; Kraehenbuhl et al., 1992; Mostov, 1994). The pIgR is important for the immunoglobulin transport into the milk. The pIgR is made by the epithelial cells of the mammary gland. This unique secretory organ produces milk, which not only provides nutritional and metabolic factors to the newborn, but also non-specific and specific antimicrobial factors such as IgA. It is generally accepted that the secretion of non-specific antimicrobial factors such as lactoferrin (Nuijens et al., 1996) and lysozyme and specific antibodies against pathogenic micro-organisms protects not only the mammary gland from infections but also the newborn. The major class of immunoglobulins in mammalian milk is IgA, which originates from B-lymphocytes emerging from mucosal sites such as Peyer's patches of the gut. The level of secretory IgA (S-IgA) depends on the lactation stage (colostrun/milk) and differs among species (Brandtzaeg, 1983; Goldblum et al., 1994).

DISCLOSURE OF THE INVENTION

The present invention provides means and methods for raising the concentration of a first class of immunoglobulin relative to at least a second class of immunoglobulin in a compartment of the body of a non-human animal or progeny thereof, the method comprising providing a cell bordering the compartment, with a nucleic acid encoding a protein capable of transporting a member of the first class of immunoglobulin from the basolateral side to the apical side of the cell. With the method, it is possible to generate animals that are better protected against invasion and/or colonization of mucosal surfaces by a pathogen. Preferably, the animal is transgenic for the nucleic acid. Offspring generated by the transgenic animal will also comprises the nucleic acid. This feature can be used to generate a large number of offspring comprising the nucleic acid. The offspring can be bred and selected for suitable characteristics. In one embodiment of the invention, this allows the generation of the transgenic animal in a line that can be more easily made transgenic. Resulting transgenic offspring can subsequently be crossed with one or more other genetic lines of the animal. Other advantages of transgenic animals comprises the selection of animals comprising the nucleic acid in a particularly favorable site in the genome of the animal. It is known in the art that the integration site in the genome influences, for instance, the longevity and the tissue preference of expression.

(A) The blot was incubated with a rabbit anti-human SC antibody and a rabbit anti-mouse IgA(a) antibody. Milk samples used: -M, non-transgenic litter mate (13 dL); line 3642 (mouse 5967, 12 dL); line 3643 (mouse 8068, 13 dL); line3644 (mouse 9507, 13 dL); line 3646 (mouse 5971, 14 dL). Dilutions used: line 3642-1:10; line 3643-1:50; line 3644-1:500; line 3646-1:200; non-transgenic litter mate-1:10. C1, purified human S-IgA from colostrum (hS-IgA, 20 ng SC). The 80 kD SC protein of the human S-IgA molecule is visible and used as a reference. C2, mouse myeloma protein IgA (MOPC 315, 30 ng). The IgA murine heavy chain is shown as a band of 60 kD. The numbers on the left indicate the molecular weight of the protein standards (kD). mSC, murine secretory component (MW 95–100 kD); mIgA (a), murine IgA heavy chain (MW 60 kD).

(B) The blot was incubated with a rabbit anti-mouse IgA(a) antibody. Milk samples used were diluted 1:10 in PBS. -M, non-transgenic litter mate (14 dL); line 3642 (mouse 8189, 12 dL); line 3643 (mouse 4779, 14 dL; mouse 8068, 13 dL); line 3644 (mouse 9507, 3 dL; mouse 9287, 12 dL); line 3646 (mouse 5971, 14 dL; mouse 10695, 12 dL). C1, purified human S-IgA from colostrum (415 kD); mS-IgA, murine secretory IgA (MW 435 kD).

Figure 9:
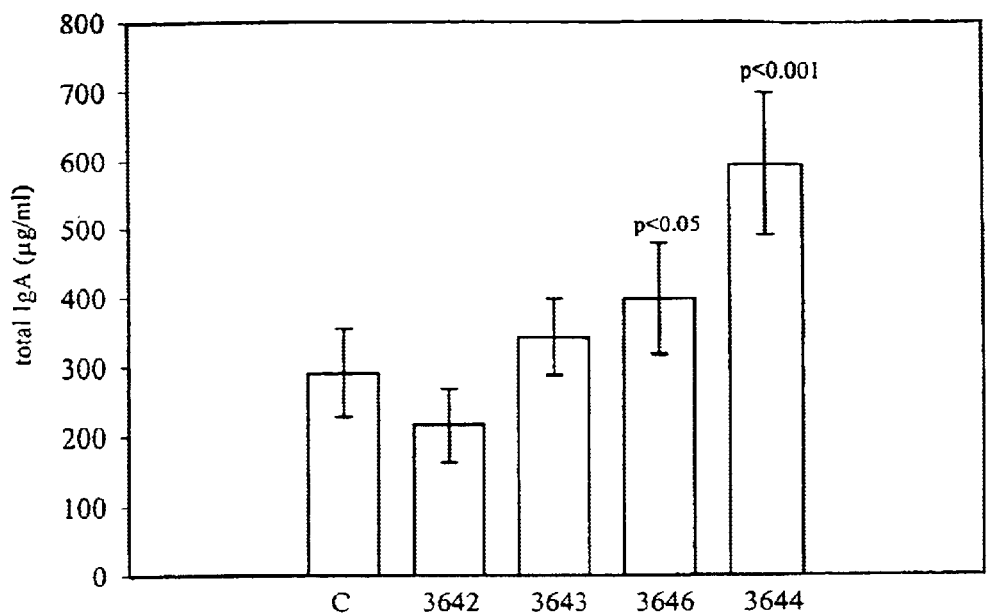
Figure 9:
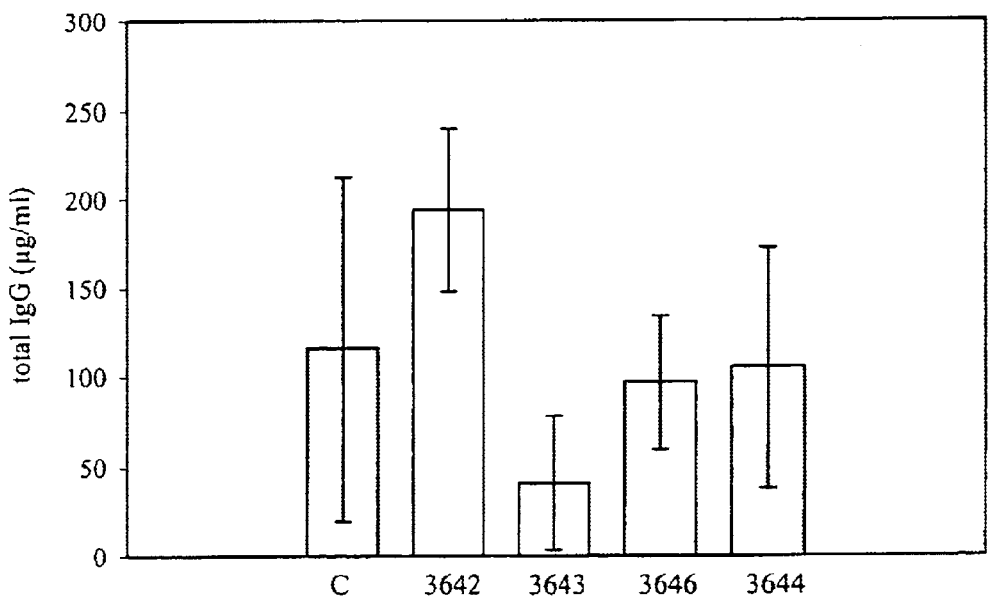

FIG. 9. Total IgA and IgG levels in the milk of pIgR transgenic mice. IgA (A) and IgG (B) levels were determined in milk samples of 5 mice per line during mid-(12–15 days) lactation by sandwich ELISA. Mean values are shown and the standard deviation is indicated. The p-value obtained via statistical analysis of the data (ANOVA) is indicated. C, control mice; transgenic line numbers: 3642, 3643, 3646 and 3644.

DETAILED DESCRIPTION OF THE INVENTION

A protein capable of transporting a member of the first class of immunoglobulin from the basolateral side to the apical side can be any receptor over expressed via for instance transgenesis or via other means, and able to transport Ig's of any kind across epithelial cells. A non limiting example of such a protein is an IgG1 receptor or functional part, derivative and/or analogue thereof (Kacskovics et al., 2000; Cianga et al, 1999; Ghetie and Ward, 2000). In a preferred embodiment of the invention, the protein comprises polymeric immunoglobulin receptor or a functional part, derivative and/or analogue thereof. Polymeric immunoglobulin receptor (pIgR) is capable of transporting dimeric IgA across epithelial cells of mucosal surfaces into the external secretions and thereby capable of raising the concentration of IgA relative to at least IgG in external secretions. A part of pIgR termed the secretory component remains associated with secreted dimeric IgA and protects the IgA from degradation in mucosal fluid. Thus additionally aiding the raise in concentration of IgA relative to at least IgG. In some animal species pIgR comprises a glycosylated transmembrane receptor protein with five extra-cellular Ig-like domains, an intra-membranous domain (Mostov et al., 1984; Eiffert et al., 1991) and a cytoplasmic domain that contains cellular sorting signals (Okamoto et al., 1992; Hirt et al., 1993; Reich et al., 1996). The protein is synthesized in the endoplasmic reticulum and routed via the Golgi complex to the basolateral side of the epithelial cells. At this side, the receptor can bind to its ligand, dIgA, secreted by local plasma cells. The receptor, instructed by various sorting signals, is endocytosed and transcytosed to the apical side of the epithelial cells with or without bound dIgA. This process is not dependent on ligand binding as shown by in vitro studies in the polarized Madin-Darby canine kidney ("MDCK") cell line (Mostov et al., 1986; Song et al., 1994) and free SC can be found in secretions (Brandtzaeg et al., 1991). At the apical side the external, N-terminal, part of the receptor protein is cleaved off to form the secretory component (SC) which remains associated to the dIgA molecule. The SC protein protects dIgA from degradation in mucosal fluids of, e.g., the gut and the mammary gland (Kraehenbuhl et al., 1992; Mostov, 1994). A functional part of pIgR comprises at least the IgA binding properties of the pIgR in kind, not necessarily in amount. To this end, the functional part preferably comprises at least one of the five extra-cellular Ig-like domains. Preferably, the functional part comprises at least three, and more preferably, at least five of the extra-cellular Ig-like domains. A functional part of the pIgR preferably further comprises the cellular sorting signals of the pIgR molecule. To this end, the functional part further comprises a part of the cytoplasmic domain of pIgR. It is not necessary to match to species of the animal with the species the pIgR protein is derived from. Preferably, the species are matched. One advantage is that immune related removal of cells is at least in part prevented. Such immune related removal of cells can for instance sometimes be a problem upon delivery of a nucleic acid encoding the protein to an immune competent animal that was previously naive for the protein.

It is not necessary to maintain all of amino acids of the pIgR intact. It is well within the skill of the artisan to introduce silent mutations in a pIgR protein, for instance through substitution with conservative amino acids. Such derivatives of pIgR are therefore also within the scope of the invention. With the knowledge of the functionality of different sections of the pIgR molecule it is possible to generate analogues molecules containing at least one of the functions of a section of pIgR. For instance, the intracellular routing function may be combined with (parts of) another immunoglobulin binding protein. Examples of such immunoglobulin binding proteins are known in the art and include protein A, protein G, Fc receptor and IgG1 receptor (Kacskovics et al., 2000; Cianga et al, 1999; Ghetie and Ward, 2000). Furthermore, other transcytoting receptors are likely to be discovered in the near future. Chimeric proteins analogues to pIgR are also within the scope of the invention.

A compartment of the body where the first class of antibody is raised can be any mucosal compartment of the body such as for instance an extra-cellular surface of a lung, an intestine, an extracellular surface of the mouth, nose and/or eye. Preferably, the compartment comprises a mammary secretion containing part of a mammary gland, such as lumen filled with milk. A cell bordering the compartment is preferably an epithelial cell. A bordering cell does not have to be completely adjacent to the compartment. It can also be separated from the compartment by one or more cell layers. However, preferably, the cell is not separated from the compartment by more than three cell layers. Preferably, the cell bordering the compartment comprises a mammary gland epithelial cell. One of the reasons for preference toward a mammary gland in the present invention is that the mammary gland is capable of excreting large amounts of secretion product. The mammary secretion products colostrum and milk comprise immunoglobulins that can be harvested and used for various purposes. Non-limiting purposes are medical and/or nutritional purposes. Whereas colostrum is relatively rich in immunoglobulin, milk is relatively poor in immunoglobulins. Considering the relatively high immunoglobulin content the colostrum would be the preferred source for harvesting immunoglobulins. However, colostrun can only be obtained from the mammary gland for two to three days following birth of a young. After that the immunoglobulin content of mammary secretion product rapidly drops. However, with the present invention it is possible to raise the immunoglobulin concentration of one Ig class relative to at least second Ig class in mammary secretion product. Thus also in milk of the animal more of a certain class of Ig, that is recognized by and transported by a protein of the invention, can be obtained, which is subsequently available for harvesting. Another reason for a preference toward a mammary gland is that mammary gland infections are a problem in commercial use of farm-animals for the production of milk. Such infection may also be at least in part prevented and/or treated by a method of the invention or in an animal of the invention.

A method of the invention can be performed with any animal. Preferably, the non-human animal is a farm-animal since farm-animals are usually housed in confined spaces and therefore more prone to pathogenic infections with bacteria and/or viruses. Preferably, the farm-animal comprise a farm-animal that is currently used for the collection of antibodies. Preferably, the farm-animal is an animal that can be milked. Preferably, the farm-animal is cow, a goat, a sheep, a camel, a lama and/or a rabbit. With a farm animal is meant any non-human animal that is in any way commercially exploited or exploitable by man.

Expression, of a nucleic acid encoding a protein capable of transporting a member of the first class of immunoglobulin from the basolateral side to the apical side of a cell, can be obtained using any means for the expression of a nucleic acid in a cell. However, preferably, the nucleic acid comprises a promoter capable of driving expression of the protein essentially specifically in the cell and/or a functional equivalent of the cell. In this way expression is essentially specific for a cell bordering the compartment and thus transport of Ig according to a method of the invention limited to the relevant cells. More preferably, the promoter is capable of expressing the protein specifically in a mammary gland cell, more preferably, an epithelial mammary gland cell.

The immunohistochemical data obtained in the present invention demonstrate that the cellular distribution and the trafficking of the receptor within the mammary gland epithelial cells of the transgenic mice are normal. In transgenic murine lines 3643, 3646 and 3644 (FIGS. 2D, E and F, respectively) staining of the receptor throughout the whole secretory epithelial cell was observed, with very dense coloring at the basolateral and apical side of the cell. This means that the transgenic receptor protein is routed to the basolateral side and to the apical side of the epithelial cell, either simultaneously or sequentially. Thus a normal transport, i.e., sequentially, of the pIgR from the basolateral side to the apical side within the epithelial cells occurs in the animals. Abnormalities in pIgR routing or intracellular deposition would lead to a discrepancy between pIgR protein levels (FIG. 7) and pIgR mRNA levels in the tissue and SC levels in the milk (FIG. 8). So, the transcytotic route of the receptor seems not to be affected by its abundant supply in lines 3646 and 3644. This, combined with the glycosylation data, which shows a normal glycosylation pattern, of the over-expressed pIgR, demonstrates that a method of the invention leads to overproduction of a functional IgA receptor.

In the milk of the lines 3646 and 3644, S-IgA is present as high MW molecules (FIG. 8B) as is the case for the low expressing lines. This high MW band has a molecular weight of 435 kD, which is the sum of two IgA dimers, J-chain, and SC. This composition was confirmed by the observation that the 435 kD complex reacts with a rabbit anti-mouse IgA antibody (FIG. 8B), a rabbit anti-human SC antibody (FIG. 4B) and a rabbit anti-human J-chain antibody (data not shown).

Results obtained for the various lines as shown on the Western blot (FIG. 3B) and those obtained by ELISA are in agreement. The lines 3646 and 3644, with the highest expression of the transgene showed a significant difference in total IgA levels, which were up to two times higher than in control milk. The increase in IgA output is not in proportion to the magnitude of the increased pIgR synthesis. The level of total IgA in milk from line 3644 was 1.5 times higher than the level in line 3646, while the SC levels in the milk were 4.5 times higher in the milk of line 3644 compared to line 3646. Thus in a preferred embodiment of the invention the cell comprises the protein in an amount that is at least 10-fold, more preferably, at least 50-fold higher than an endogenously expressed analogous and/or homologous immunoglobulin transporter protein. More preferably, the cell comprises the protein in an amount that is at least 100-fold higher than an endogenously expresses analogous and/or homologous inmmunoglobulin transporter protein.

In one aspect, the invention provides a method of the invention further comprising inducing and/or amplifying an antigen specific immunity in the animal. Preferably, the antigen specific immunity is induced and/or amplified through administering the antigen or a functional part, derivative and/or analogue thereof to the animal. Preferably, the administration is such that a mucosal immune response is obtained. Antigen specific immunity may also be induced and/or amplified through grafting of antigen specific immunoglobulin producing cells in the animal. Upon inducing and/or amplifying an antigen specific immune response in the animal much more antigen specific immunoglobulins of the first class are found in the compartment than before the induction and/or amplification. A raise of the concentration of antigen specific immunoglobulins of the first class is significantly higher than in antigen immunized animals, not treated with a method of the invention.

In another aspect, the invention provides a non-human animal wherein a cell of the animal comprises a recombinant nucleic acid encoding a protein capable of transporting an immunoglobulin from the basolateral side to the apical side of the cell. Such an animal can be used to produce more immunoglobulin, preferably (d)IgA as a product. Non limiting applications of such a product are medical applications for man and animals. Preferably, the animal is generated with a method of the invention. Preferably, the animal is transgenic for the recombinant nucleic acid.

In yet another aspect, the invention provides secretory fluid obtainable from a non-human animal of the invention. Preferably, the secretory fluid comprises saliva, milk, tears, urine or other body fluids. Preferably, the secretory fluid comprises milk.

The invention further provides a method for collecting an immunoglobulin from a non-human animal, preferably a farm-animal, comprising providing an excretory cell of the animal with a nucleic acid encoding a protein capable of transporting the immunoglobulin from the basolateral side to the apical side of the cell, the method further comprising collecting excretory fluid produced by the cell and/or the tissue the cell is a part of, and obtaining the immunoglobulin. In one aspect, the invention thus also provides the use of a method of the invention or a animal of the invention for obtaining a composition comprising an immunoglobulin.

In yet another aspect, the invention provides of a method of the invention further comprising administering to the animal or a part thereof, a substance capable of enhancing expression of the protein. Expression of proteins can be induced in various ways. One can for instance use inducible promoters and supply the inducing substance for the promoter. A non-limiting example of such a couple is a steroid hormone substance and a steroid hormone inducible promoter. Likewise so for promoters inducible controlled by lactogenic substances including hormones. However, it is also possible to use normal promoters and enhance expression through providing the promoter with a substance that is capable of affecting the expression of many different promoters in a general way, for instance through causing demethylation of the nucleic acid. A non-limiting example of such a substance is butyrate. In a preferred aspect of the invention, the substance comprises interferon-g, interleukin-1, interleukin-4 and/or tumor necrosis factor-a. Several studies have shown up-regulation of the pIgR by IFN-g, interleukin-1, interleukin-4 and/or tumor necrosis factor-a (Kvale et al., 1988; Phillips et al., 1990; Piskurich et al., 1993; Hayashi et al., 1997). Also natural or artificial genes encoding these proteins can be used. For introduction of these genes, transgenic or other methods known to those skilled in the art can be used (e.g., for instance gene gun methods, DNA vaccination methods, Gene therapy methods, viral vehicles and other transsomatic methods).

EXAMPLES

Materials and Methods
Construction of the Murine pIgR Expression Cassettes

Figure 1:
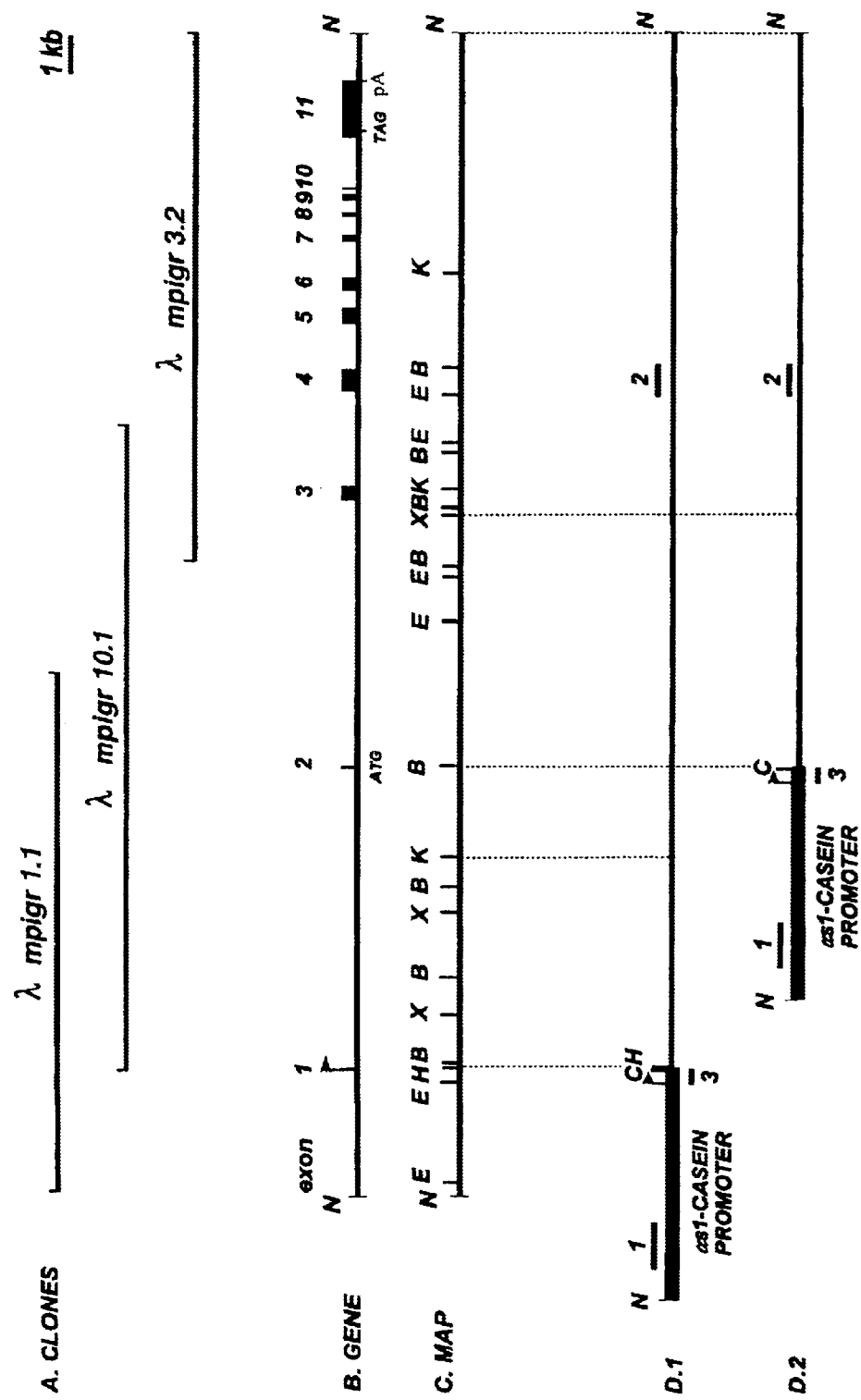
FIG. 1: The structure of the murine pIgR gene and construction of two expression cassettes. (A) The three clones obtained from the mouse genomic library. The sizes are: 1 mpigr 1.1: 13.5 kb; 1 mpigr 10.1: 16.5 kb; 1 mpigr 3.2: 13.5 kb. (B) The exon-intron organization. The exons are numbered 1 through 11 and the translation start and stop signals are indicated. The total length of the isolated gene is 30.2 kb, with a 3.1 kb promoter region, 24.4 kb exon-intron area, 1.4 kb 3' UTR and 1.3 kb 3'flank. The sizes of exon 1 to 11 are: 124, 99, 345, 654, 333, 333, 193, 128, 132, 59 and 1489 bp, respectively. The approximate sizes of intron 1 to 10 are: 7.8, 6.9, 2.4, 1.2, 0.5, 1.0, 0.4, 0.4, 0.1 and 1.3 kb, respectively. ©) The restriction map of the pIgR gene. The different restriction enzymes are indicated: E, EcoRI; B, BamHI; X, XhoI; K, KpnI; H, HindIII; N, NotI. (D) Construction of the expression cassettes. (D.1) In construct c1pIgRE1, the regulatory sequences of the bovine $a_{s1}$-casein gene were fused via an introduced ClaI ©) site to the HindIII (H) site within the first exon of the murine pIgR gene. (D.2) In construct c2pIgRE2 these regulatory sequences were fused via an introduced ClaI ©) site to the second exon of the murine pIgR gene. Probes used in DNA and RNA analysis are numbered 1, 2 and 3, see, Materials and Methods.

A genomic library constructed with genomic liver DNA of mouse strain 129 in lambdaGEM®-12 cloning vector (gift from Prof. dr. A. Berns, NKI, Amsterdam) was screened using murine pIgR cDNA (Piskurich et al., 1995) (gift from Dr. C. S. Kaetzel, Case Western University, USA). Three positive clones were identified containing the whole pIgR gene on overlapping fragments (FIG. 1A). The three clones were analyzed by extensive restriction mapping and sequence analysis (FIG. 1B, 1C). Sequence analysis was performed by using the T7seqencing™ kit (Pharmacia), based on the dideoxy chain-termination method (Sanger et al., 1977).

Two expression cassettes were constructed that contained the pIgR gene but lacked its promoter region. Instead, the pIgR gene was fused to the bovine $a_{s1}$-casein regulatory sequences via an introduced ClaI site (Platenburg et al., 1994). In the first expression cassette exon1, intron1 and the first 31 nt of exon2 of the pIgR gene were lacking (FIG. 1D.2). The ClaI site was introduced 25 nt upstream of the translation start site (Genebank no. Y16524) of the pIgR gene via PCR directed mutagenesis of the 2.3 kb KpnI-BamHI fragment (FIG. 1C). The PCR fragment containing the ClaI site was subcloned into the pCR™II vector (Invitrogen) by TA cloning and sequenced to confirm its identity. Next, the ClaI-BamHI (127 bp) fragment was isolated from this vector and fused to the BamHI-XhoI fragment (6.7 kb). The resulting ClaI-XhoI fragment was ligated into a pKUN based vector (Konings et al., 1987) behind the bovine $a_{s1}$-casein regulatory sequences (6.3 kb) using the ClaI and XhoI sites. In the final step, the NotI-XhoI fragment (13 kb), containing the $a_{s1}$-casein regulatory sequences and the modified exon 2 region, and the XhoI-NotI fragment (12.5 kb), containing exon 3 to 11 and the 3' flanking sequences, were ligated into dephosphorylated NotI digested pWE15 cosmid vector, resulting in cosmid c2pIgRE2.

The second expression cassette contained the complete murine pIgR gene (FIG. 1D.1), starting from a ClaI restriction site introduced 45 bp downstream of the transcription start site (Genebank no. Y16523). The ClaI site was inserted in two cloning steps. First, the 5.6 kb HindIII-KpnI fragment (FIG. 1C) was inserted into the pBluescript®II KS (+/−) phagemid (Stratagene). In the second step, a linker sequence (NotI-EcoRV-ClaI-HindIII) was inserted into this vector using the NotI and HindIII sites in the polylinker resulting in the fusion of the linker to the 5.6 kb HindIII-KpnI fragment. In the final step, the excised ClaI-KpnI fragment and the KpnI-XhoI fragment (9 kb) were ligated into the cosmid vector pWE15, containing the bovine $a_{s1}$-casein regulatory sequences and the XhoI-NotI fragment (12.5 kb), resulting in cosmid 1pIgRE1. Both expression cassettes were checked by sequencing of the exons, intron-exon borders, 3' untranslated region (3' UTR) and 5' UTR (Sanger et al., 1977).

Generation of Transgenic Mice

The 25.5 kb (c2pIgRE2) and 33.4 kb (c1pIgRE1) DNA fragments containing the pIgR transgene were released from the pWE15 cosmid by NotI digestion and purified by agarose gel electrophoresis and electroelution. The DNA was microinjected into fertilized BCBA (C57Bl/6×CBA/J) mouse eggs and the eggs were reimplanted into pseudopregnant females (Hogan et al., 1986; Pinkert, 1994). The mice were housed at the transgenic mouse facility, University Medical Center Leiden, the Netherlands.

Southern Blot Analysis of the Transgenic Mice

The integration of the constructs was identified by EcoRI digestion of genomic DNA extracted from tail biopsies (Laird et al., 1991). DNA fragments were separated on a 0.7% agarose gel and blotted on Hybond™-N+ (Amersham). Transgene integration, integrity and copy number were determined using a 1.3 kb HindIII-KpnI fragment located at the 5' end of the bovine $a_{s1}$-casein regulatory sequences (probe 1, FIG. 1D) and a 0.8 kb EcoRI-BamHI fragment located near the 3' end of the pIgR gene (probe 2, FIG. 1D). These probes were labeled with [a-$^{32}$P] dCTP (3000 Ci/mmol, ICN) using the random primer DNA labeling kit (Gibco BRL). Transgene copy numbers were estimated by comparing the hybridization signal to the signal obtained with an amount of purified plasmid DNA equivalent to 1, 5 or 10 copies of the gene mixed with genomic tail DNA from non-transgenic mice.

PCR Analysis of the Transgenic Mice.

PCR analysis of tail DNA was performed with the upstream primer corresponding to a 16 bp sequence in the bovine $a_{s1}$-casein promoter region (5'-CTTGGGAGAGGAACTG-3' (SEQ ID NO: 1)) and the downstream primer corresponding to a 21 bp sequence in exon 1 (5'-AGCTACTTCCTTCTCTCCAGG-3' (SEQ ID NO: 2)) or a 21 bp sequence in exon 2 (5'-AAGACAGTTACCAAGAGCGTG-3' (SEQ ID NO: 3)) of the pIgR gene. A PCR product of 234 bp was generated after 30 cycles (1 minute 94° C., minute 47° C., 1 minute 72° C.) in case integration of the c2pIgRE2 construct. A PCR product of 244 bp was generated after 30 cycles (1 minute 94° C., 1 minute 50° C., 1 minute 72° C.) in case of integration of the c1pIgRE1 construct. The PCR was performed in 50 ml containing 1 ml of tail DNA, 1.0 unit of Goldstar Red DNA polymerase (Eurogentec), reaction buffer (75 mM Tris-HCl, pH 9.0, 20 mM (NH4)2SO4, 0.01% (w/v) TWEEN 20, 1.0 mM MgCl2; Eurogentec), 0.5 mM of each primer and 0.2 mM dNTP (Gibco).

Total RNA was extracted from the mammary gland and seven other tissues (heart, spleen, liver, intestine, salivary gland, kidney and uterus) using TRIzol Reagent (Gibco BRL) (Chomczynski et al., 1987). Transgene expression was measured at 8 or 12 days during the lactation stage. Northern blot analysis was performed according to standard protocols (Sambrook et al., 1989). Briefly, the RNA preparations were separated by electrophoresis under denaturing conditions in a 0.7% agarose MOPS/formaldehyde gel and transferred from the gel to Hybond™-N+ membrane (Amersham) by downward alkaline capillary blotting for 4 hours (Chomczynski, 1992). After blotting, the membranes were pre-hybridized for 30 minutes in hybridization solution (0.125M Na2HPO4, 0.25M NaCl, 1.0 mM EDTA, 7% SDS, 10% PEG 6000) with herring sperm DNA (Promega), followed by hybridization for 2 hours at 65° C. The hybridization temperature for the synthetic oligonucleotide was 45° C. The probes were labeled with [a-$^{32}$P] dCTP (3000 Ci/mmol, ICN) using the random primer DNA labeling kit (Gibco BRL). The synthetic oligonucleotide was labeled with [g-$^{32}$P] dATP (4500 Ci/mmol, ICN) using T4 polynucleotide kinase (Pharmacia). RNA blots were probed with an oligonucleotide (5'-ATCGATGGGTTGATGATCAAGGTGATGG-3' (SEQ ID NO: 4)) corresponding to the complementary sequence of the bovine $a_{s1}$-casein 5'UTR (exon 1) to determine the expression level of the transgene (probe 3, FIG. 1D). Endogenous expression of the murine pIgR gene together with the transgene expression was measured with the murine pIgR cDNA (3095 bp) (Piskurich et al., 1995). Endogenous expression of a milk protein gene was measured with a 200-bp EcoRI-PstI murine b-casein cDNA fragment (Hennighausen et al., 1982). To correct for RNA loading differences, blots were hybridized with a 1.4 kb human 28S ribosomal probe. The transcription levels of the pIgR transgene in the different mouse lines were compared with the endogenous pIgR levels by measuring the hybridization signal with a Betascope 603 Blot Analyzer (Westburg b.v., the Netherlands).

Collecting Milk Samples from Mice

Milk samples were collected at various time-points during lactation, early (day 3–5), mid (day 6–14) and late (day 15–19) lactation. From each transgenic line three mice were used to collect the milk samples. The mothers were separated from their pups for 2–3 hours before milking and injected subcutaneously with 1.0 unit of oxytocin-S (Intervet, Boxmeer, NL) (diluted 1:1 in PBS) 10 minutes before milking. The milk was collected with a vacuum pump device and stored at –20° C.

Analysis of the Milk by SDS/PAGE and Western Blotting

Milk samples were diluted (1:10) in PBS and equal volumes (2 ml) of the se dilutions were loaded under reducing and non-reducing conditions onto a 7.5% SDS/PAGE gel. The milk of non-transgenic mice was used to measure the endogenous level of the pIgR protein. Purified human S-IgA from pooled human colostrum (Sigma) was used as a control. SDS/PAGE and Western blotting were performed according to standard protocols (Laemmli, 1970; Sambrook et al., 1989) using the mini-PROTEAN II Cell and PVDF-0.2 mm membrane (Bio-Rad Laboratories). After blotting, the membranes were blocked for 1 hour in TBS (pH 7.5) containing 0.2% TWEEN-20 (Sigma) and 5% nonfat milk powder (Protifar; Nutricia). As first antibody a polyclonal rabbit anti-human secretory component (Dako), diluted 1:1000 in 0.2% TWEEN-20 and 1% Protifar in TBS (pH 7.5) was used. Peroxidase-conjugated swine anti-rabbit IgG, diluted 1:1000 in 0.2% TWEEN-20 and 1% Protifar in TBS (pH 7.5) was used as second antibody. The first antibody was incubated overnight at room temperature and the second antibody for 1 hour at room temperature. Enhanced chemiluminescence (ECL) detection was performed using Na-luminol (Sigma) and p-Coumaric acid (Sigma) (Thorpe et al., 1986). The amount of SC in the milk of the transgenic mice was quantified by densitometric analysis of the blots with the UVISoft Windows application V.97 (UVITech), using known amounts of human SC (S-IgA; Sigma) as a reference. SDS-PAGE gels were stained with Coomassie-Brilliant-Blue R-250 to reveal the protein bands.

SC and IgA Detection in the Milk by Western Blotting

Milk samples were diluted in PBS and the samples were loaded under reducing conditions onto 7.5% SDS/PAGE gels. The milk of non-transgenic mice was used to measure the endogenous SC and IgA levels. Purified human S-IgA from pooled human colostrum (Sigma) and mouse myeloma protein IgA (12) (ICN) were used as control. SDS/PAGE and Western blotting were performed according to standard protocols (Laemmli, 1970; Sambrook et al, 1989) using the mini-PROTEAN II Cell system and PVDF membrane (Bio-Rad). After blotting, the membranes were blocked for 1 hour in TBST (100 mM Tris-HCl pH 7.5/150 mM NaCl/0.2% (v/v) TWEEN-20 (Sigma)) containing 5% (w/v) non-fat milk powder (Protifar; Nutricia). For detection of the SC protein a rabbit anti-human SC (Dako) was used and a rabbit anti-mouse IgA antibody (ICN) was used for detection of the IgA heavy chain. Both antibodies were diluted 1:1000 in TBST containing 1% Protifar. Peroxidase-conjugated, sheep anti-rabbit IgG (ICN) diluted 1:10000 in TBST containing 1% Protifar, was used as second antibody in all cases. The first antibody was incubated overnight at room temperature (RT) and the second antibody for 1 hour at RT. Enhanced chemiluminescence detection (Thorpe and Kricka, 1986) was performed using Na-luminol and p-Coumaric acid (Sigma).

Deglycosylation of SC Protein

Milk samples (1 ml), containing approximately 100 mg of total protein as determined with the BCA Protein Assay Kit (Pierce), were denatured by heating for 5 minutes at 100° C. after adding 25 ml 0.1M b-mercaptoethanol/0.5% SDS. Next, 50 ml containing 25 ml 0.5M Tris-HCl (pH 8.0), 10 ml 10% non-ionic detergent (NP-40, ICN) and 1 ml (1U) N-Glycosidase F (Boehringer Mannheim) was added to each denatured milk sample. The same reagents were added to the control, but without enzyme. The samples were incubated overnight at 35° C. for complete deglycosylation. Milk samples were heated for 5 minutes at 100° C. to inactivate N-Glycosidase F. Milk proteins were separated on a 7.5% SDS/PAGE gel and SC was detected as described for western blotting.

Immunohistochemical Localization of pIgR Protein

Mammary gland tissues from mice of all transgenic lines were fixed in 4% paraformaldehyde and embedded in paraffin. Sections were cut (5 mm) and placed on APES-treated glass slides. Tissues were deparaffinated and endogenous peroxidase activity was blocked by incubation for 20 minutes in methanol/0.3% (v/v) $H_2O_2$. Next, tissues were rehydrated in 100%, 70% and 50% ethanol, washed two times for 5 minutes with PBS. As a first antibody rabbit anti-human SC (1:200; Dako) in PBS/1% bovine serum albumin (BSA) was used and incubated overnight in a moist chamber. Slides were washed three times for 5 minutes with PBS and incubated for 30 minutes in a moist chamber with a biotinylated swine anti-rabbit antibody (1:400; Dako), as secondary antibody in PBS/1% BSA/10% normal mouse serum. Slides were washed three times for 5 minutes with PBS and incubated for 30 minutes in a moist chamber with a biotinylated HRP/Streptavidin complex (Dako). As a peroxidase substrate DAB (Sigma) was used. All sections were counter stained with haematoxyline.

Measuring IgA and IgG Levels in the Milk by ELISA

Milk from 5 mice per transgenic line was collected during the mid-lactation period. Purified mouse IgA (2; ICN) and mouse IgG (Sigma) was used as a standard for measuring IgA and IgG levels, respectively, in the milk samples. ELISA was performed according to standard protocols (Cowther, 1995). Briefly, microtiterplates (Greiner) were coated overnight at 4° C. with an affinity purified goat anti-mouse IgA (a) antibody (0.5 mg/ml; ICN) or an affinity purified goat anti-mouse IgG Fc antibody (2 mg/ml; ICN) in 0.1M sodium carbonate buffer (pH 9.6) for the IgA or IgG ELISA respectively. After four washes with PBS the wells were blocked with PBS/0.05% TWEEN-20/0.25% BSA (Sigma) (PBS-TWEEN-BSA) for 30 minutes at 37° C. Milk samples diluted in PBS-TWEEN-BSA were added to the wells. Plates were incubated during each step for 1.5 hours at 37° C. and washed three times with PBS. The goat anti-mouse IgA (a) and the goat anti-mouse IgG Fc were also used conjugated with biotin-NHS (Boehringer Mannheim), diluted 1:4000 in PBS-TWEEN-BSA. HRP-labeled Streptavidin (Amersham), diluted 1:1000 in PBS-TWEEN-BSA, was added to the wells and incubated for 30 minutes at 37° C. Detection of the peroxidase was performed with OPD (o-phenylenediamine dihydrochloride, 0.5 mg/ml; Sigma) as a substrate in phosphate-citrate buffer (pH 5.0). The coloring reaction was stopped after 15 minutes with 3M HCl. Optical densities were measured at 490 nm using a Universal Microplate Reader ELx800 (Bio-Tek Instruments). The ANOVA test was used for statistical analysis.

RESULTS

Isolation of the Murine pIgR Gene and Generation of Transgenic Mice

A genomic library of mouse strain 129 was screened using murine pIgR cDNA (Piskurich et al., 1995) as a probe. Three clones, named mpigr 1.1 (13.5 kb), mpigr 10 (16.5 kb) and mpigr 3.2 (13.5 kb), were identified, containing the whole pIgR gene on overlapping fragments (FIG. 1A). The complete murine pIgR gene was analyzed by restriction mapping (FIG. 1B, 1C) and sequencing (GeneBank no. Y16523-Y16532). For the generation of transgenic mice two expression cassettes were constructed, which contained the bovine $a_{s1}$-casein regulatory sequences (Platenburg et al., 1994) fused to the pIgR gene via an introduced ClaI site (see, FIG. 1D and Materials and Methods). The 3' UTR and 1.3 kb of 3' flanking sequences of the pIgR gene were used in both expression cassettes. The 3' region was analyzed by sequencing and the polyadenylation site was found 1393 bp downstream of the translation stop codon (see, GeneBank no. Y16532).

Transgenic mice were generated via separate microinjection of the 25.5 kb (c2pIgRE2) and the 33.4 kb (c1pIgRE1) NotI fragments. Southern blotting and PCR were used to identify the transgenic mice. Transgene integrity and copy numbers were determined by Southern blotting. Five founder animals harboring the 25.5 kb pIgR transgene were generated and lines were established for each of these founders. All lines contained intact copies of the pIgR construct and copy numbers of the transgene varied between 1 to 5–10 copies per cell. Five founder animals harboring the 33.4 kb pIgR transgene were generated and lines were established for each of these founders. Four lines contained intact copies of the pIgR construct with copy numbers varying from 1 to more than 10 copies per cell. Founder number 3645 did not transmit the transgene. In line 3646 the transgene was transmitted to 100% of the first generation and among these mice two different transgene copy numbers were found, indicating two integration sites. This line was continued with two F1 mice, which transmitted intact copies of the transgene to half of their offspring, indicating that only one integration site was present.

Transcription of the Murine pIgR Transgene in the Mammary Gland

Figure 2:
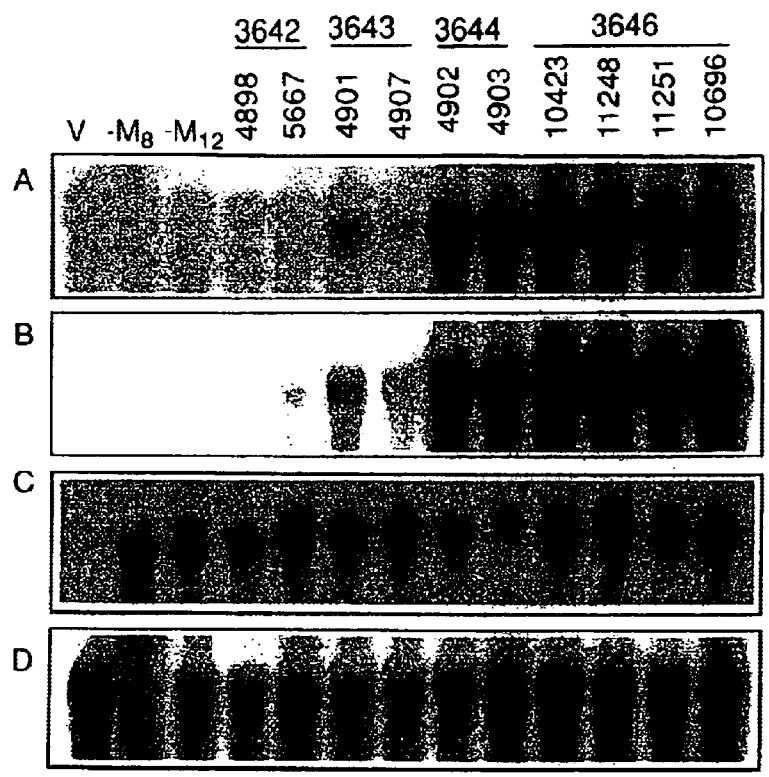
FIG. 2: Relative transcript levels of the pIgR transgene in the mammary gland. Northern blot analysis of total RNA (20 mg/lane) isolated from mammary gland tissue (day 8 or 12 of lactation) of transgenic F1 females of the different lines. Blots were hybridized to: a 28 nt probe complementary to the 5' UTR of the transgene (A; probe 3, FIG. 1D), murine pIgR cDNA (B), murine b-casein cDNA (C), human 28S ribosomal RNA probe (D). Mammary gland RNA samples: V, virgin transgenic mouse (line 3643; mouse 8678); -M, non-transgenic litter mate (8 or 12 days); line 3642 (mouse 4898, day 8 and mouse 5667, day 12); line 3643 (mouse 4901, day 8 and mouse 4907, day 12); line 3644 (mouse 4902, day 8 and mouse 4903, day 12) and line 3646 (mouse 10423, day 8 and mouse 11248, day 12; mouse 11251, day 8 and mouse 10696, day 12).

Total RNA was isolated from mammary gland tissue of transgenic F1 female mice 8 or 12 days after onset of lactation. The expression level of the transgene and its transcript size were determined by Northern blotting. The transgene specific mRNA expression was determined by using a synthetic oligonucleotide complementary to the 5'UTR of the bovine $a_{s1}$-casein gene (exon 1) and the engineered ClaI site (probe 3, FIG. 1D). A murine pIgR cDNA probe (Piskurich et al., 1995) was used to measure the mRNA expression level of the transgene, as compared to the endogenous pIgR expression. The expression of the 25.5 kb (c2pIgRE2) transgene was measured using the oligonucleotide, but none of the five lines showed any transgene specific mRNA expression. The mRNA levels measured did not exceed the endogenous pIgR mRNA level, indicating that the transgene was not transcribed (data not shown). Specific expression levels of the 33.4 kb (c1pIgRE1) transgene were also measured using the oligonucleotide. Correctly sized transgene specific transcripts were present in all the four lines carrying intact copies of the transgene (FIG. 2). The size of these transcripts was identical to the size of the endogenous murine pIgR mRNA (3.9 kb). The full-length pIgR mRNA, as determined by sequence analysis and genomic organization studies, was calculated to be 3895 bp excluding the 3' poly (A) tail (data not shown). The transgene derived transcript levels were compared to the expression level of the endogenous pIgR gene in the mammary gland of a non-transgenic mouse at the same lactation periods by quantification of the hybridization signals. In the mammary gland of virgin transgenic mice (line 3646) no transgene specific transcript was detected, indicating that transgene expression only occurs after onset of lactation. Furthermore, endogenous expression of the murine b-casein gene was not present in these virgin mice, confirming a non-developed mammary gland (FIG. 2C). Line 3642 with one transgene copy per cell showed a low mRNA expression level. Line 3643, containing 2–5 transgene copies per cell, expressed the gene at a level approximately 10 times higher than the endogenous expression. Line 3646, containing 2–5 transgene copies per cell, expressed the gene at a level approximately 30 times higher than the endogenous mRNA expression level. Line 3644, containing more than 10 copies of the transgene, expressed the gene more than 30 times higher as compared to the endogenous mRNA expression level of the pIgR. Results are summarized in Table 1.

Tissue Specificity of pIgR Transgene Expression

Figure 3:
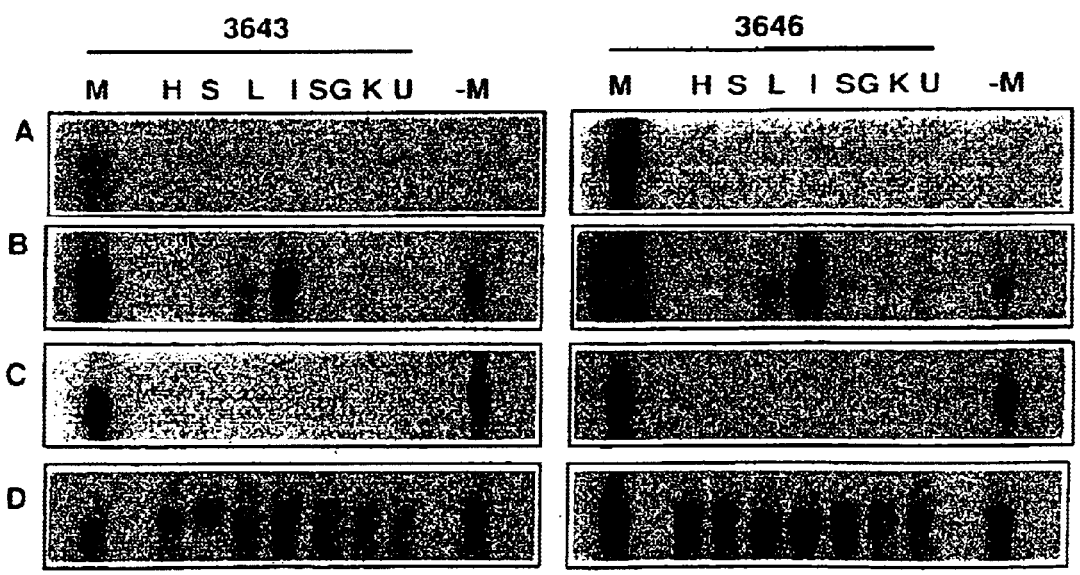
FIG. 3: Tissue specificity of the pIgR transgene expression. Northern blot analysis of total RNA (20 mg/lane) from seven different tissues of two independently generated transgenic mouse lines: 3643 (mouse 4901, day 8) and 3646 (mouse 10696, day 12). Tissues analyzed: H, heart; S, spleen; L, liver, I, intestine; SG, salivary gland; K, kidney; U, uterus; M, mammary gland; -M, mammary gland of a non-transgenic litter mate (day 12). Blots were hybridized to: a 28 nt probe complementary to the 5' UTR of the transgene (A; probe 3, FIG. 1D), murine pIgR cDNA (B), murine b-casein cDNA ©), human 28S ribosomal RNA probe (D).

Tissue specificity of the transgene expression was determined by Northern blot analysis of total RNA from seven different tissues (heart, spleen, liver, intestine, salivary gland, kidney, uterus) and from the mammary gland tissue of two mice at day 8 or 12 of lactation of each transgenic line of construct c1pIgRE1. Expression of the transgene was exclusively found in the lactating mammary gland in all lines. This resembles the tissue specificity of the milk protein b-casein gene, which was detected only in lactating mammary gland tissue. Endogenous expression of the murine pIgR gene was detected in the liver, intestine and mammary gland, but not in heart and spleen. Low expression levels were detected in the salivary gland, kidney and uterus. Results for line 3643 (mouse 4901, day 8) and line 3646 (mouse 10696, day 12) are shown in FIG. 3.

Amount of SC Protein in the Milk of Transgenic Mice

Figure 4:
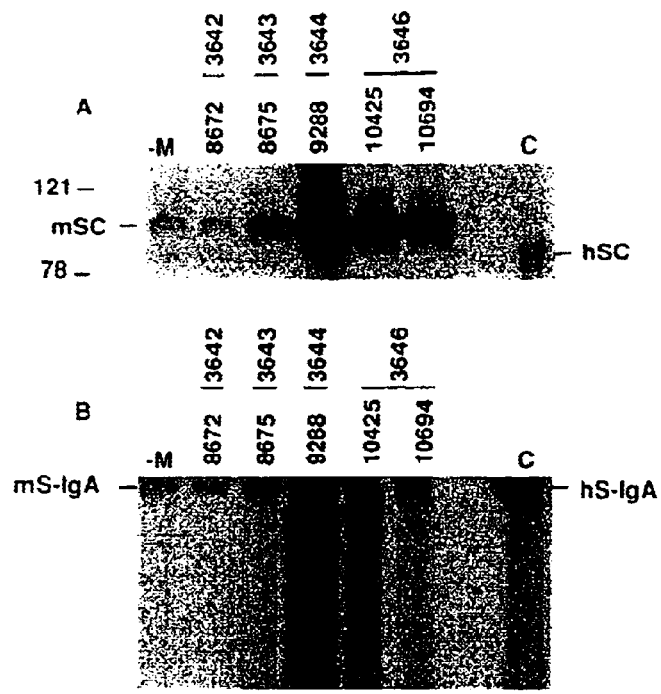
FIG. 4: SC levels in the milk of transgenic mice. Western blot analysis of milk samples from transgenic F2 females of the various mouse lines. Milk samples were diluted 1:10 with PBS and 2 ml of each sample was loaded under reducing conditions (A) or non-reducing conditions (B) on a 7.5% SDS/PAGE gel. Milk samples: -M, non-transgenic litter mate (day 11); line 3642 (mouse 8672, day 10); line 3643 (mouse 8675, day 12); line 3644 (mouse 9288, day 11); line 33646 (mouse 10425, day 11 and mouse 10694, day 12); C, purified human IgA from colostrum (hS-IgA; 20 ng SC) containing the human SC (80 kD) was used as a reference. mSC, murine secretory component; hSC, human secretory component; mS-IgA, murine secretory IgA; hS-IgA, human secretory IgA. The numbers on the left indicate the molecular weight of the protein standards (kD).

The SC protein level was measured in the milk of transgenic F2 female mice of all four lines of construct c1pIgRE1. Milk samples were collected throughout lactation (early, day 3–5; mid, 6–14; late, 15–19) from three mice per line. Equal amounts of diluted mouse milk samples (1:10 in PBS) were fractionated by SDS/PAGE under reducing and non-reducing conditions. The SC protein was visualized by Western blotting using a polyclonal rabbit antibody directed against human SC, which cross-reacts with the murine SC protein (FIG. 4). SDS/PAGE under reducing conditions revealed that all transgenic lines expressing the pIgR gene in their mammary gland, secreted the SC protein with a molecular weight (MW) of 95–100 kD in their milk (FIG. 4A). The amount of SC protein in the transgenic mouse milk samples was quantified by comparison to known amounts of purified human SC protein (MW 80 kD) and was compared to the endogenous SC levels in normal milk under reduced conditions (Table 1-protein level: Midlactation). Line 3646 produced the SC protein at a level 60 times higher than the endogenous SC protein level and the amount of SC protein in line 3644 was 270 times higher than the endogenous SC protein level. The protein level in line 3643 was 10 times higher and line 3642 produced amounts of SC not significantly above the level of the endogenous protein in milk of non-transgenic mice.

SDS/PAGE under non-reducing conditions revealed a strong SC band complexed with dIgA (murine S-IgA: MW 435 kD; human S-IgA: MW 415 kD) in the milk of the transgenic mice (FIG. 4B). Milk of the non-transgenic mice contained no free SC suggesting that there is sufficient dIgA to form a complex with the SC. Milk samples of transgenic line 3642 did not show free SC indicating that also in this case all SC was bound to dIgA. However, lines 3643, 3644 and 3646, which produced much more receptor mRNA as compared to the non-transgenic mice and also much higher amounts of SC in their milk, showed high amounts of free SC not bound to dIgA. Remarkably, the levels of the S-IgA complex appeared to be elevated in the lines 3643, 3644 and 3646, which produce the highest amount of receptor protein.

Figure 5:
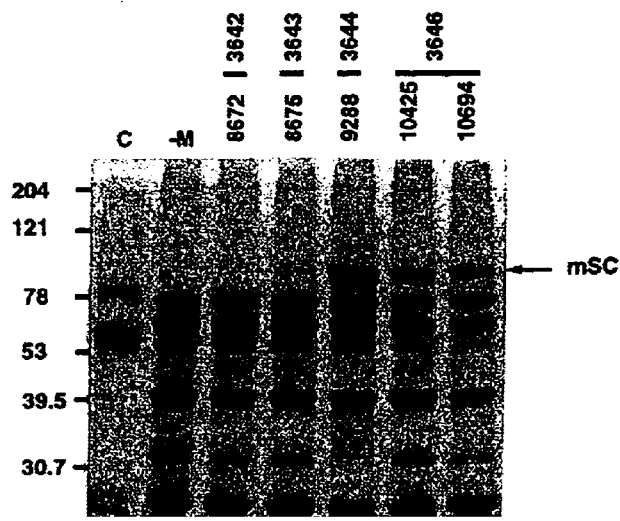
FIG. 5: Protein composition of transgenic mouse milk. Milk samples were diluted 1:10 in PBS and 2 ml of each sample was loaded under reducing conditions onto a SDS/PAGE gel (10%) and stained for total protein. Milk samples: C, purified human IgA from colostrum (hS-IgA; 15 mg) as reference, showing human SC band (80 kD), the IgA heavy chain (60 kD), the light chain (20 kD) and the J-chain (15 kD but migrates like a 25 kD protein); -M, non-transgenic litter mate (day 11); line 3642 (mouse 8672, day 10); line 3643 (mouse 8675, day 12); line 3644 (mouse 9288, day 11); line 3646 (mouse 10425, day 11 and mouse 10694, day 12). mSC, murine secretory component. The numbers on the left indicate the molecular weight of the protein standards (kD).

The protein composition in the milk of the transgenic lines was compared to that of a non-transgenic mouse. Protein samples were separated on a 10% SDS/PAGE gel and stained with Coomassie-Brilliant Blue (CBB) (FIG. 5). The caseins, a1 (MW 43 kD), b (MW 26 kD) and g ($a_{s2}$-like; MW 23.7 kD) were identified (Hennighausen et al., 1982; Stevenson et al., 1994). The two higher bands could represent lactoferrin (MW 78 kD) and milk serum albumin (MW 67 kD) of the mouse (Hennighausen et al., 1982). In the milk of the non-transgenic mouse a faint band of the endogenous SC protein was detected at the position where the transgenic lines (3644, 3646) show a strong band (MW 100–95 kD). This band contains the murine SC protein resulting from the over-expression of the pIgR transgene.

SC and mRNA Levels in pIgR Transgenic Mice

Four transgenic lines were generated containing the complete murine pIgR gene under the control of the bovine $a_{s1}$-casein regulatory sequences (de Groot et al, 1999). In all four lines, the transgene was exclusively expressed in the mammary gland. Transgene copy numbers ranged from 1 to >10 copies/cell. The pIgR mRNA levels in the mammary gland tissue differed among the transgenic lines. Accordingly, varying amounts of SC protein were found in the milk of all lines analyzed. Line 3644, containing the highest copy number (>10) of the transgene, showed mRNA levels 30 times higher compared to the endogenous gene in non-transgenic mice. The SC levels in the milk of this line were elevated more than 250-fold resulting in levels of 2.7–2.8 mg/ml compared to 0.01 mg/ml in non-transgenic control mice. Line 3646 (2–5 copies/cell) expressed the pIgR gene at mRNA levels 30 times higher as compared to the endogenous gene in non-transgenic mice. The SC levels in the milk of these mice were 0.6–0.8 mg/ml. In line 3643 (2–5 copies/cell) mRNA levels were 10 times higher as compared to endogenous mRNA expression and SC levels reached 0.1–0.3 mg/ml. In line 3642 (1 copy/cell) the mRNA levels were low and the SC levels in the milk were equal to those found in the milk of non-transgenic control mice.

Glycosylation of the Extracellular Part of Murine pIgR Protein

Previous studies have demonstrated that rat (Sztul et al, 1985; Musil et al, 1987), human (Purkayastha et al, 1979; Mizoguchi et al, 1982; Mostov and Blobel, 1982; Elkon, 1984; Eiffert et al, 1991), rabbit (Solari and Kraehenbuhl, 1984; Frutiger et al, 1988) and bovine (Labib et al, 1976) pIgR molecules are N-glycosylated. Furthermore, an in vitro study with murine pIgR cDNA stably transfected into Chinese hamster ovary cells showed that the murine pIgR is also glycosylated (Asano et al, 1998). Potential sites for N-glycosylation with the consensus sequence Asn-X-Ser/Thr (Kornfeld and Kornfeld, 1985) are present for mouse, rat, human, rabbit and bovine pIgR. For the murine pIgR eight such sites were found in the extracellular domains 1, 2, 4 and 5 of the receptor (Piskurich et al, 1995). In case of human Eiffert et al, 1991) and rabbit (Frutiger et al, 1988) pIgR, all consensus sites are indeed glycosylated. The potential N-glycosylation sites vary among the species and some sites are more conserved than others (Piskurich et al, 1995).

Figure 6:
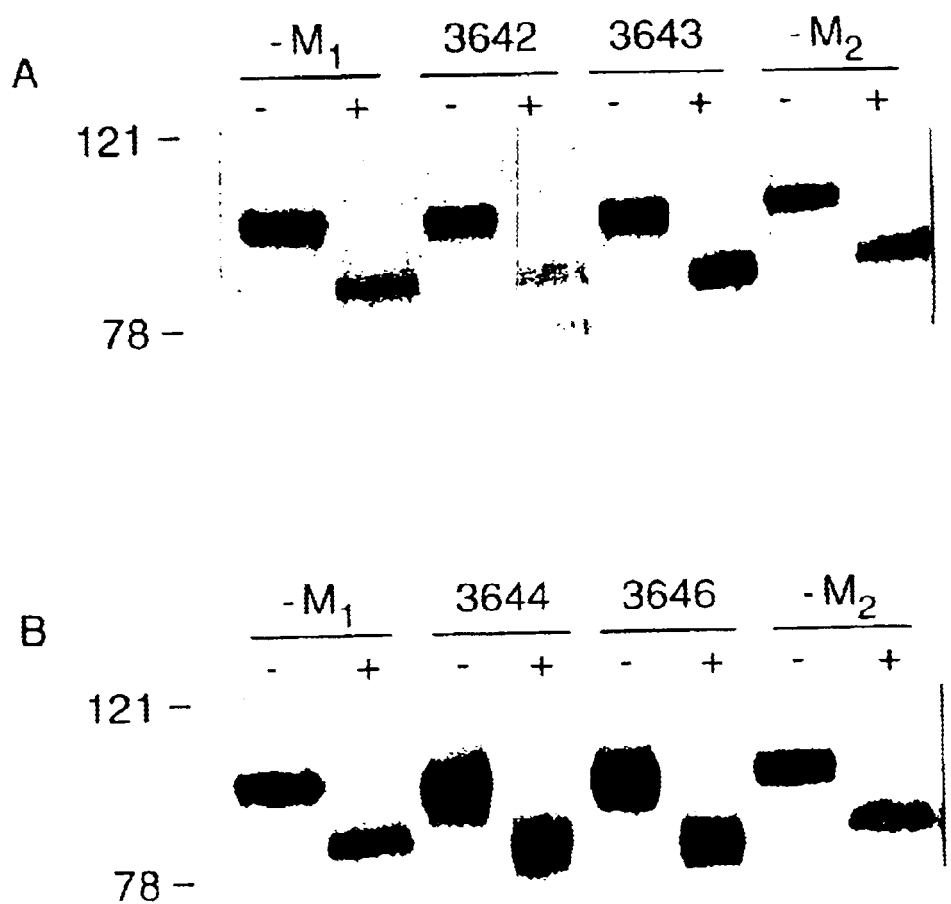
FIG. 6. Glycosylation of the murine SC protein. Western blot analysis of milk samples from F2 females of four transgenic lines. Milk samples (1 ml) were treated with (+) or without (−) N-Glycosidase F (1U) and separated on a 7.5% SDS/PAGE gel. The SC protein has a MW of 95–100 kD; the deglycosylated form has a MW of 80–85 kD. Control milk samples: -M1, non-transgenic litter mate (mouse 9726, 13 days lactation (dL)); -M2, non-transgenic litter mate (mouse 9714, 11 dL). Milk samples: (A) line 3642 (mouse 8189, 12dL); line 3643 (mouse 4779, 14 dL). (B) line 3644 (mouse 9507, 11 dL); line 3646 (mouse 4769, 13 dL). Molecular weight markers are indicated on the left (kD).

In order to rule out that overproduction of the receptor, especially in the lines with a 60 to 270 fold overproduction, might lead to incomplete glycosylation we examined the presence of N-linked oligosaccharide chains in the transgenic SC protein. Incomplete glycosylation could be due to insufficient glycosylation capacity of the epithelial cells in case of lines 3646 and 3644. This could have a negative impact on the functionality of the pIgR protein with respect to IgA transport. The presence of N-linked oligosaccharide chains in the transgenic SC protein (95–100 kD) was examined in these lines by deglycosylation followed by immunoblotting with a rabbit anti-human SC antibody. After deglycosylation, one protein band, approximately 15 kD less in molecular weight, around 80–85kD was found in all transgenic lines as well as in the control mice (FIG. 6). In all cases only one SC band was found showing uniformity in the degree of N-glycosylation regardless the pIgR expression level. This suggests that no aberrant glycosylation has taken place as a consequence of over-expressing the pIgR. When calculating the degree of N-linked glycosylation, using a MW of approximately 1.5–3 kD for an average N-linked carbohydrate chain, 5 to 10 sugar chains must be present in the extracellular part of the endogenous and the transgenic pIgR. This estimation is in agreement with the eight potential glycosylation sites present in the murine SC protein.

Figure 7:
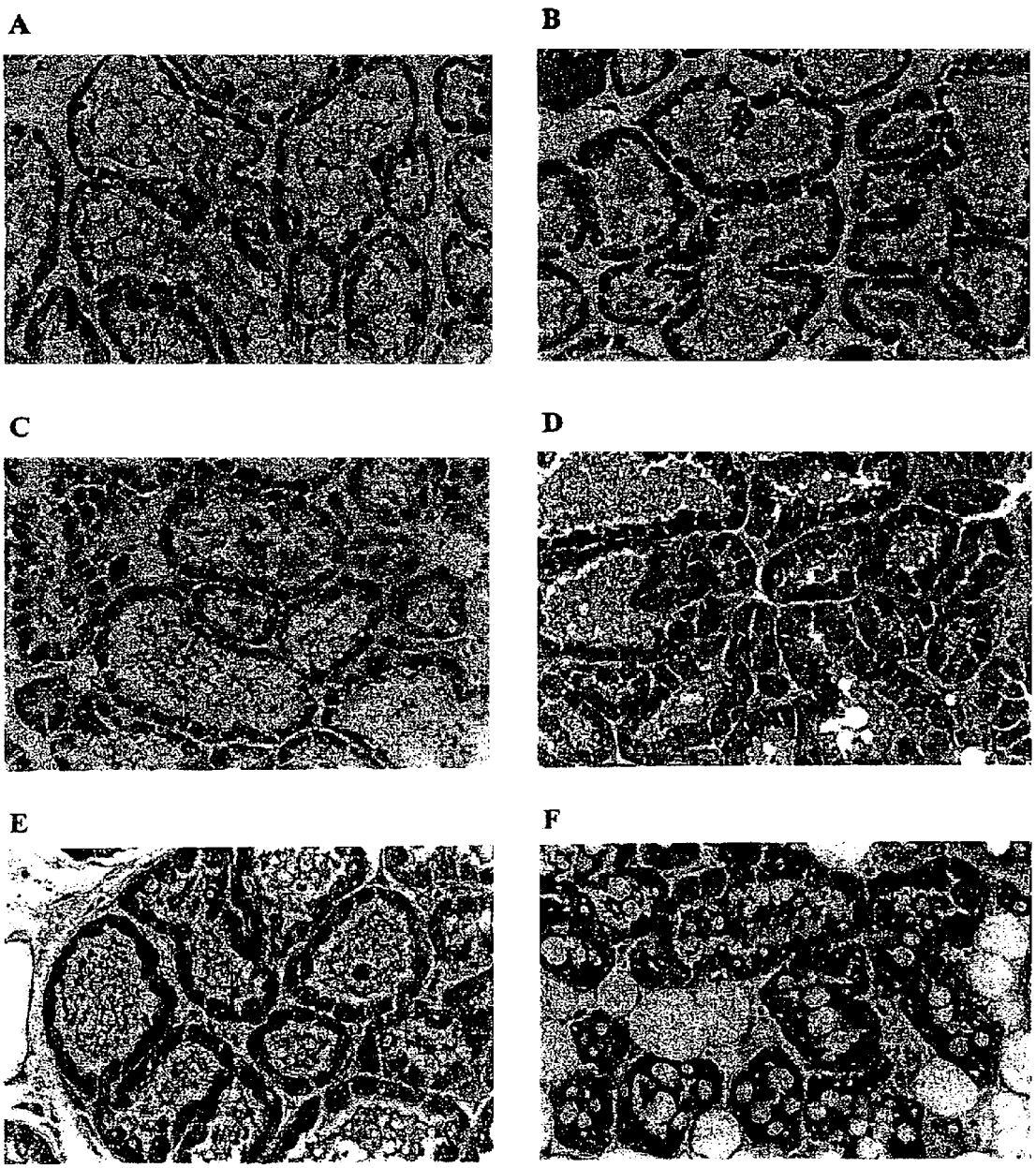
FIG. 7. Intracellular and extracellular localization of the pIgR protein in the mammary gland. Mammary gland tissue from mice of all transgenic lines was isolated at day 12 of lactation and tissue sections were incubated with a rabbit anti-human SC antibody. This antibody cross-reacts with the murine SC protein. (A) Mammary gland tissue of line 3646 incubated with PBS as a negative control. (B) a non-transgenic litter mate to detect the endogenous pIgR expression in the epithelial cells of the mammary gland. The secretory epithelial cells of the alveoli show specific pIgR staining in the lines 3642 (C), 3643 (D), 3646 (E) and 3644 (F).
Figure 8:
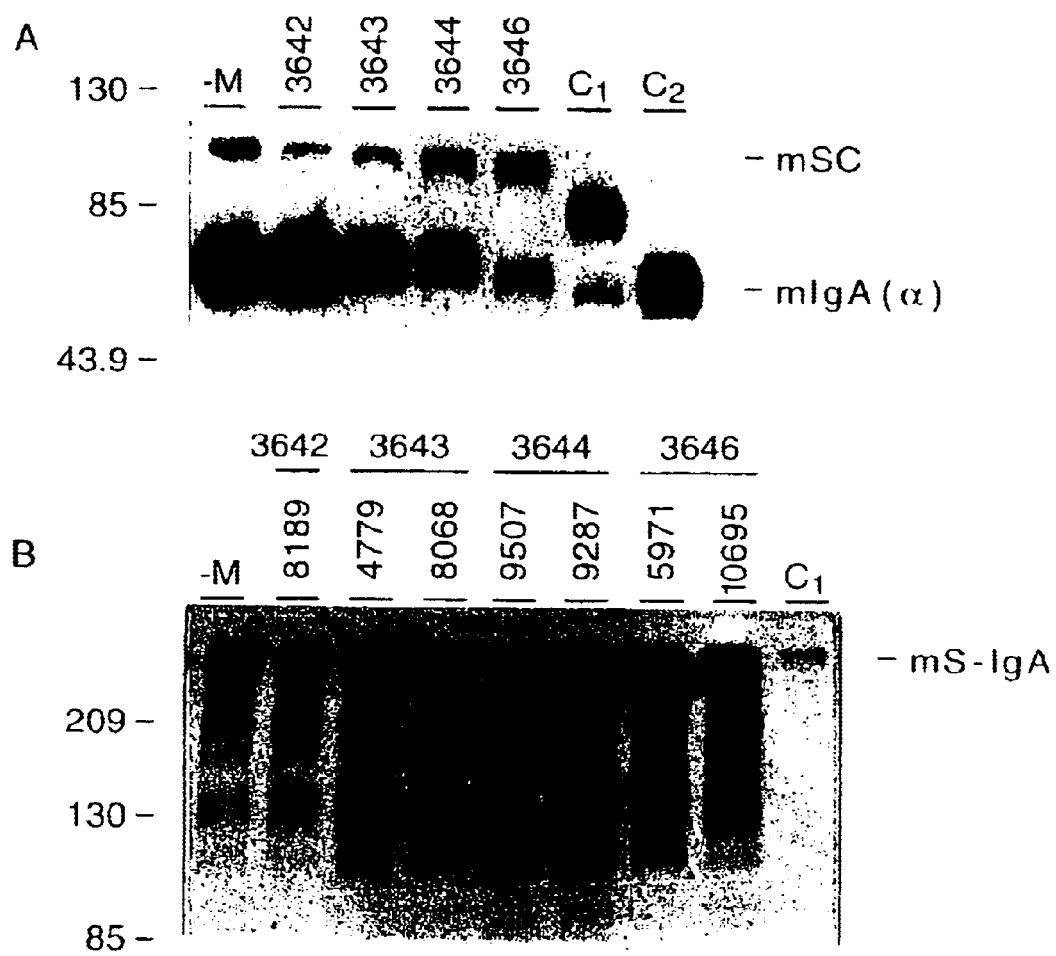
FIG. 8. IgA and SC in the milk of transgenic mice. Western blot analysis of milk samples, collected from F2 female mice of all transgenic lines. Samples were diluted in PBS as indicated below and 3 ml was fractionated on a 7.5% SDS/PAGE gel under reducing conditions (A) or non-reducing conditions (B).

Immunohistochemical Localization of the pIgR Protein in Mammary Gland Tissue Sections Localization of the pIgR protein in the epithelial cells was shown by immunohistochemical analysis of mammary tissue sections from all the transgenic lines (FIG. 7). The endogenous pIgR protein is visible in the alveolar and ductal epithelial cells of the mammary gland of non-transgenic mice as shown by the light brownish color of these cells (FIG. 7B). The milk in the lumen of the alveoli is also stained, which shows that the SC protein is secreted into the milk. In all the transgenic lines the pIgR protein is found in the secretory epithelial cells of the alveoli and the ducts. The pIgR transgene is homogeneously expressed in the epithelial cells throughout the whole mammary gland tissue in all lines. Staining is strong at the basolateral and the apical side of the epithelial cells (FIGS. 7D, E and F). This indicates that transport of the receptor takes place to both the basolateral and the apical side of the epithelial cell. In the lines 3643, 3646 and 3644 (FIGS. 7D, E and F) the epithelial cells are much stronger stained at the apical side of the cells than at the basolateral side. This might indicate that the receptor release at the apical side is relatively slow, suggesting that proteolytic cleavage is limiting. The milk in the lumen of the alveoli is also strongly stained, which must be due to free SC or SC bound to dIgA (FIG. 7F). Line 3644 also shows the highest SC protein levels in the milk as measured by Western blotting (FIG. 8). Lines 3643 and 3646 also have high pIgR levels (FIGS. 7D and E, respectively), but much less than in line 3644.In the single copy line (3642) we found a low pIgR level in the epithelial cells given the light brown coloring of the cells (FIG. 7C). In all cases the milk in the lumen of the alveoli was also stained. The intensity of the pIgR protein staining is in proportion to the SC levels in the milk (see, FIG. 8).

Determination of IgA Levels in pIgR Transgenic Mice.

We have obtained transgenic mice with a strongly increased level of pIgR in the mammary gland. We have demonstrated that transgene expression takes place exclusively within the epithelial cells, that the receptor is localized at the proper locations within the cells and that the receptor has a complete N-glycosylation profile. Now that the epithelial cells are equipped with an excess of functional receptor protein, we are in the position to ask the question whether or not such an increased amount of pIgR leads to elevated IgA levels in the milk.

The IgA levels were determined on SDS/PAGE gels under reducing (FIG. 8A) and non-reducing (FIG. 8B) conditions with a rabbit anti-mouse IgA antibody. Underreducing conditions, IgA heavy chain was found as a 60 kD band in all the transgenic lines and in the control group (FIG. 8A). Under non-reducing conditions, IgA polymers corresponding to the MW of S-IgA molecules (murine S-IgA: MW 435 kD; human S-IgA: MW 415 kD) were found. The bands with lower MW, are most likely caused by dissociation of a portion of S-IgA during SDS/PAGE (Parr et al, 1995). In line 3644 clearly more S-IgA is present (FIG. 8B). Total IgA levels were determined by ELISA in the milk of all four transgenic lines during mid-lactation (FIG. 9A). In the milk of the non-transgenic control group, the mean value of total IgA was 292 mg/ml. Transgenic line 3642 showed total IgA levels similar to the control group. In the milk from mice of line 3643, which have a 10-fold higher SC level in their milk than control mice, the total IgA level was increased slightly (FIG. 9A). Line 3646, having a 60-fold elevated SC protein level in the milk, showed 1.5 times elevated IgA levels. In line 3644, which has a 270-fold increased SC level, the concentration of total IgA was doubled (593 mg/ml) compared to the IgA concentration found in the milk of control mice. This shows that in the line with the highest pIgR expression, more IgA is transported across the epithelial cells into the milk.

The pIgR transports IgA but not IgG. In order to demonstrate that the effect is specific for the pIgR and not a general immunological phenomenon, we also measured the IgG levels in the milk of these mice. The levels were not significantly different from the IgG levels found in the milk of non-transgenic mice (FIG. 9B). This proves that the over-expressed IgA receptor does not influence the IgG transport system into the milk. We conclude that elevated pIgR levels are enhancing IgA uptake and transport selectively.

Determination of Antigen Specific IgA in Milk

BCBA mice (lines 3642, 3643, 3644 and 3646 were used; non transgenic mice served as control) were immunized with a Vibrio cholera based vaccine supplemented with recombinant CTB which was purchased from the vendor (SBL Sweden). Pregnant female mice were rectally immunized.

The immunization method was adopted to mice and was essentially as described by Kato et al Vaccine 2000 18 (13) 1151–60; see, also Kozlowski et al Infect. Immun. 1997 65 (4) 1387–94. Other mucosal immunization methods (made more suitable for other animal species) and methods as known to those skilled in the art can also be applied resulting in qualitatively similar effects in the pIgR transgenic mice.

After parturition, some of the milk was collected and the total amounts of IgA in milk were determined as described in de Groot et al 1999.

The milk samples were processed as described by de Groot et al, and the proteins were separated on a PAGE gel and subjected to western blotting using an antibody against IgA to visualize the IgA H and L chain and to determine in a semi-quantitative manner the relative IgA levels in immunized transgenic mice versus the non-immunized transgenic mice.

Immunization of the control mice leads to detectable increase of IgA levels compared to the specific pathogen free mice as previously described by us. Whereas in the spf mice transgenic strain 3642, 3643, 3646 and 3644 the relative IgA levels are 1.0; 1.0; 1, 5 and 2.0 respectively (see, ref 12) the IgA levels are considerably higher when these strains are mucosally immunized viz. 1.0; 2.5; 5.0 and 5.0 respectively.

These results show that the total IgA levels can be increased also in the mice overexpressing the receptor ten fold dine 3643) and that the IgA output is further enhanced in mice overexpressing this receptor even further (line 3646 and 3644) 5 times. A more than 100 fold increase in receptor expression does not further enhance the IgA output (line 3644 vs 3646) indicating that in these mice IgA synthesis, rather than pIgR levels, has become rate limiting.

Alternatively, and to complement the previous experiment, mice (the control and mice from the transgenic lines 3642, 3643, 3644 and 3646) were given a backpack tumor according to method known to those skilled in the art (see, Apter et al Infect Immun. 1993 December 61 (12): 5279–85 and Marandi and Mittal Infect. Immun. 1997 November 65 (11) 4502–08. These hybridoma proliferate and secrete one type of antibody of the secretory IgA class and directed against cholera toxin. It concerns an antibody that needs the pIgR to be transported to mucosal tissues among which the mammary gland. Milk was collected as described above. CT specific monoclonal IgA levels were measured in the milk. In the control mice the relative level, in ELISA units, of monoclonal IgA is set at one. In the transgenic mice of line 3643 these levels were about 2 fold higher and in line 3646 these levels were about 10 fold higher. A further increase in pIgR levels as in line 3644 did not further increase these IgA levels.

In the present invention, we report for the first time expression of a transmembrane receptor molecule at very high levels in the mammary gland. The total amount of SC protein in the milk of transgenic mice ranged from 0.1 to 2.7 mg/ml, which is 10 to 270 times higher than the level in control milk. The pIgR mRNA expression levels in these mice seemed to be correlated to the transgene copy number. This demonstrates that expression was independent of the integration site of the transgene in the mouse genome.

The first construct (c1pIgRE1) used to generate transgenic lines contained the complete murine pIgR gene. The second construct (c2pIgRE2) lacked exon 1, intron 1 and part of exon 2 (see, Materials and Methods). None of the lines generated with the c2pIgRE2 construct showed any transgene mRNA expression in their mammary glands in contrast with the transgene expression found in the lines from the c1pIgRE1 construct. The difference between both pIgR constructs at the level of transcription is at least in part due to the lack of intron 1. Intron 1 in the pIgR gene contains elements that control its expression as a transgene and perhaps also its expression as an endogenous gene. Line 3642, containing the lowest amount of SC in the milk, showed that all SC was bound to dIgA (FIG. 4B). This indicates that all pIgR molecules produced by the epithelial cells are used for the transcytosis of dIgA. The three lines having much higher amounts of total SC in the milk (lines 3643, 3644 and 3646), showed that a large fraction of the total amount of SC protein was in free form. This demonstrates that many of the receptor molecules are transcytosed through the epithelial cell layer without ligand. In comparison to the normal mouse, the amount of IgA bound to SC seemed to be higher in the lines 3643, 3644 and 3646 (FIG. 4B). The additional bands as shown in FIG. 4B might be complexes of SC with other forms of IgA or milk proteins.

The present invention demonstrates that in vivo in case of abundance of the pIgR relative to the amount of dIgA, the receptor is transported without ligand and cleaved to form free SC.

TABLE 1

Transgene expression at mRNA and protein level in 5 independent pIgR transgenic mouse lines.

| Line | Copy no. | Relative RNA levels[a] | Range of SC protein level (mg/ml)[b] | |
|---|---|---|---|---|
| | | | mid-lactation | max. level |
| wt | — | – | 0.01 | 0.04 |
| 3642 | 1 | + | 0.01 | 0.02 |
| 3643 | 2–5 | ++ | 0.1 | 0.3 |
| 3646 | 2–5 | +++ | 0.6 | 0.8 |
| 3644 | >10 | ++++ | 2.7 | 2.8 |
| 3645 | — | – | — | — |

[a]Relative RNA expression levels in mammary gland tissue of female transgenic mice at 8 or 12 days of lactation as indicated by: (+) low; (++) intermediate; (+++) high and (++++) very high.
[b]Amount of total SC protein in the milk of transgenic mice measured during the mid-lactation (6–14 days) period; mean value of three female mice per line. The amount of SC in the milk was estimated by comparison with known amounts of human SC. Maximal level: represents the highest amount of total SC observed in the milk of three female mice per line.

References

Asano M, Saito M, Fujita H, Wada M, Kobayashi K, Vaerman J-P, Moro I. Molecular maturation and functional expression of mouse polymeric immunoglobulin receptor. J. Immunol. Methods 1998; 214: 131–39.

Brandtzaeg, P. (1983) The secretory immune system of lactating human mammary glands compared with other exocrine organs. Ann. NY Acad. Sci. 409, 353–383.

Brandtzaeg, P., Nilssen, D. E., Rognum, T. O. and Thrane, P. S. (1991) Ontogeny of the mucosal immune system and IgA deficiency. Gastroenterol. Clin. North Am. 20, 397–439.

Brem, G., Hartl, P., Besenfelder, U., Wolf, E., Zinovieva, N. and Pfaller, R. (1994) Expression of synthetic cDNA sequences encoding human insulin-like growth factor-1 (IGF-1) in the mammary gland of transgenic rabbits. Gene 149, 351–5.

Bijvoet, A. G. A., Kroos, M. A., Pieper, F. R., van der Vliet, M., de Boer, H. A., van der Ploeg, A. T., Verbeet, M. Ph. and Reuser, A. J. J. (1998) Recombinant human acid a-glucosidase: high level production in mouse milk, biochemical characteristics, correction of enzyme deficiency in GSDII KO mice. Hum. Mol. Genet. 7, 1815–24.

Childers, N. K., Bruce, M. G. and McGhee, J. R. (1989) Molecular mechanisms of immunoglobulin A defense. Annu. Rev. Microbiol. 43, 503–36.

Chomczynski, P. and Sacchi, N. (1987) Single-step method of RNA isolation by acid guanidinium thiocyanate-phenol-chloroform extraction. Anal. Biochem. 162, 156–9.

Chomczynski, P. (1992) One-hour downward alkaline capillary transfer for blotting of DNA and RNA. Anal. Biochem. 201, 134–9.

In Cianga et al., (1999). Identification and function of neonatal Fc receptor in mammary gland of lactating mice. Eur. J. of Immunol Vol 29(8) 2515–23.

Crowther J R. ELISA: Theory and Practice. In: Methods in Molecular Biology. Vol. 42, Totowa, N J; Humana Press Inc: J M Walker, 1995.

de Groot N, van Kuik-Romeijn P, Verbeet MPh, Vollebregt E, Lee S H, de Boer HA Over-expression of the murine polymeric immunoglobulin receptor gene in the mammary gland of transgenic mice. Transgenic Res. 1999; 8: 125–35. Erratum Transgenic Res. 1999; 8: 319.

Eiffert, H., Quentin, E., Wiederhold, M., Hillemeir, S., Decker, J., Weber, M. and Hilschmann, N. (1991) Determination of the molecular structure of the human free secretory component. Biol. Chem. Hoppe-Seyler 372, 119–28.

Elkon K B. Charge heterogeneity of human secretory component: immunoglobulin and lectin binding studies. Immunol. 1984; 53: 131–39.

Frutiger S, Hughes G J, Hanly W C, Jaton J-C. Rabbit secretory components of different allotypes vary in their carbohydrate content and their sites of N-linked glycosylation. J. Biol. Chem. 1988; 263: 8120–25.

Ghetie V and Ward E S (2000). Multiple roles of the major histocompatibility complex class 1 related FcRn. Annu Rev. Immunol. Vol. 18:739–66.

Goldblum, R. M. and Goldman, A. S. (1994) Immunological components of milk: formation and function. Goldblum, R. M., Goldman, A. S., Ogra, P. L., Lamm, M. E., McGhee, J. R., Mestecky, J., Strober W. and Bienenstock, J. (eds), Handbook of Mucosal Immunology, p.643–52. New York: Academic Press.

Hayashi, M., Takenouchi, N., Asano, M., Kato, M., Tsurumachi, T., Saito, T. and Moro, I. (1997) The polymeric immunoglobulin receptor (secretory component) in a human intestinal epithelial cell line is up-regulated by interleukin-1. Immunol. 92, 220–5.

Hennighausen, L. G. and Sippel, A. E. (1982) Characterization and cloning of the mRNAs specific for the lactating mouse mammary gland. Eur. J. Biochem. 125, 131–41.

Hirt, R. P., Hughes, G. J., Frutiger, S., Michetti, P., Perregaux, C., Poulain-Godefroy, O., Jeanguenat, N., Neutra, M. R. and Kraehenbuhl, J-P. (1993) Transcytosis of the polymeric Ig receptor requires phosphorylation of serine 664 in the absence but not the presence of dimeric IgA. Cell 74, 245–55.

Hogan, B., Costantini, F. and Lacy, E. (1986) Manipulating the Mouse Embryo: A Laboratory Manual. Cold Spring Harbor, N.Y.: Cold Spring Harbor Laboratory Press.

P A Kacskovics et al. (2000) Cloning and characterization of the bovine MHC class I-like Fc receptor. J. Immunol 15; 164(4):1889–97.

Kaetzel, C. S., Robinson, J. K., Chintalacharuvu, K. R., Vaerman, J-P. and Lamm, M. E. (1991) The polymeric immunoglobulin receptor (secretory component) mediates transport of immune complexes across epithelial cells: A local defense function for IgA. Proc. Natl. Acad. Sci. USA 88, 8796–800.

Konings, R. N., Verhoeven, E. J. and Peeters, B. P. (1987) pKUN, vectors for the separate production of both DNA strands of recombinant plasmids. Methods Enzymol. 153, 12–34.

Kornfeld R, Kornfeld S. Assembly of asparagine-linked oligosaccharides. Ann. Rev. Biochem. 1985; 54: 631–64.

Kraehenbuhl, J-P. and Neutra, M. R. (1992) Molecular and cellular basis of immune protection of mucosal surfaces. Phys. Rev. 72, 853–79.

Krajci, P., Solberg, R., Sandberg, M., Oyen, O., Jahnsen, T. and Brandtzaeg, P. (1989) Molecular cloning of the human transmembrane secretory component (poly-Ig receptor) and its mRNA expression in human tissues. Biochem. Biophys. Res. Commun. 158, 783–9.

Kvale, D., Lovhaug, D., Sollid, L. M. and Brandtzaeg, P. (1988) Tumor necrosis factor-a up-regulates expression of secretory component, the epithelial receptor for polymeric immunoglobulins. J. Immunol. 140, 3086–9.

Labib R S, Calvanico N J, Tomasi T B. Bovine secretory component. Isolation, molecular size and shape, composition, and $NH_2$-terminal amino acid sequence. J. Biol. Chem. 1976; 251: 1969–74.

Laemmli, U. K. (1970) Cleavage of structural proteins during the assembly of the head of bacteriophage T4. Nature 227, 680–5.

Laird, P. W., Zijderveld, A., Linders, K., Rudnicki, M. A., Jaenisch, R. and Berns, A. (1991) Simplified mammalian DNA isolation procedure. Nucleic Acids Res. 19, 4293.

Lamm, M. E. (1997) Interaction of antigens and antibodies at mucosal surfaces. Annu. Rev. Microbiol. 51, 311–40.

Mazanec, M. B., Kaetzel, C. S., Lamm, M. E., Fletcher, D. and Nedrud, J. G. (1992) Intracellular neutralization of virus by immunoglobulin A antibodies. Proc. Natl. Acad. Sci. USA 89, 6901–5.

Mazanec, M. B., Nedrud, J. G., Kaetzel, C. S. and Lamm, M. E. (1993) A three-tiered view of the role of IgA in mucosal defense. Immunol. Today 14, 430–5.

Meade, H., Gates, L., Lacy, E. and Lonberg, N. (1990) Bovine alphas1-casein gene sequences direct high level expression of active human urokinase in mouse milk. Bio/Technology 8, 443–6.

Mizoguchi A, Mizuochi T, Kobata A. Structures of the carbohydrate moieties of secretory component purified from human milk. J. Biol. Chem. 1982; 257:9612–21.

Mostov, K. E., Friedlander, M. and Blobel, G. (1984) The receptor for transepithelial transport of IgA and IgM contains multiple immunoglobulin-like domains. Nature 308, 37–43.

Mostov K E, Blobel G. A transmembrane precursor of secretory component. The receptor for transcellular transport of polymeric immunoglobulins. J. Biol. Chem. 1982; 257: 11816–21.

Mostov, K. E. and Deitcher, D. L. (1986) Polymeric immunoglobulin receptor expressed in MDCK cells transcytoses IgA. Cell 46, 613–21.

Mostov, K. E. (1994) Transepithelial transport of immunoglobulins. Annu. Rev. Immunol. 12, 63–84.

Musil L S, Baenziger J U. Intracellular transport and processing of secretory component in cultured rat hepatocytes. Gastroenterol. 1987; 93: 1194–1204.

Nuijens, J. H., van Berkel, P. H. C. and Schanbacher, F. L. (1996) Structure and biological actions of lactoferrin. J. Mammary Gland Biology and Neoplasia 1, 285–95.

Okamoto, C. T., Shia, S-P., Bird, C., Mostov, K. E. and Roth, M. G. (1992) The cytoplasmic domain of the polymeric immunoglobulin receptor contains two internalization signals that are distinct from its basolateral sorting signal. J. Biol. Chem. 267, 9925–32.

Parr, E. L., Bozzola, J. J. and Parr, M. B. (1995) Purification and measurement of secretory IgA in mouse milk. J. Immunol. Methods 180, 147–57.

Phillips, J. O., Everson, M. P., Moldoveanu, Z., Lue, C. and Mestecky, J. (1990) Synergistic effect of IL-4 and IFN-g on the expression of polymeric Ig receptor (secretory component) and IgA binding by human epithelial cells. J. Immunol. 145, 1740–4.

Pinkert, C. A. (1994) Transgenic Animal Technology: A Laboratory Handbook. San Diego: Academic Press, Inc.

Piskurich, J. F., France, J. A., Tamer, C. M., Willmer, C. A., Kaetzel, C. S. and Kaetzel, D. M. (1993) Interferon-g induces polymeric immunoglobulin receptor mRNA in human intestinal epithelial cell by a protein synthesis dependent mechanism. Mol. Immunol. 30, 413–421.

Piskurich, J. F., Blanchard, M. H., Youngman, K. R., France, J. A. and Kaetzel, C. S. (1995) Molecular cloning of the mouse polymeric Ig receptor. Functional regions of the molecule are conserved among five mammalian species. J. Immunol. 154, 1735–47.

Platenburg, G. J., Kootwijk, E. P. A., Kooiman, P. M., Woloshuk, S. L., Nuijens, J. H., Krimpenfort, P. J. A., Pieper, F. R., de Boer, H. A. and Strijker, R. (1994) Expression of human lactoferrin in milk of transgenic mice. Transgenic Res. 3, 99–108.

Purkayastha S, Rao C V N, Lamm M E. Structure of the carbohydrate chain of free secretory component from human milk. J. Biol. Chem. 1979; 254: 6583–87.

Reich, V., Mostov, K. and Aroeti, B. (1996) The basolateral sorting signal of the polymeric immunoglobulin receptor contains two functional domains. J. Cell Sci. 109, 2133–9.

Rijnkels, M., Kooiman, P. M., Platenburg, G. J., van Dixhoorn, M., Nuijens, J. H., de Boer, H. A. and Pieper, F. R. (1995) High-level expression of the bovine $a_{s1}$-casein gene in milk of transgenic mice. Transgenic Res. 6, 1–10.

Sambrook, J., Fritsch, E. F. and Maniatis, T. (1989) Molecular Cloning: A Laboratory Manual. Cold Spring Harbor, N.Y.: Cold Spring Harbor Laboratory Press.

Sanger, F., Nicklen, S. and Coulson, A. R. (1977) DNA sequencing with chain-terminating inhibitors. Proc. Natl. Acad. Sci. USA 74, 5463–7.

Solari R, Kraehenbuhl J-P. Biosynthesis of the IgA antibody receptor: A model for the transepithelial sorting of a membrane glycoprotein. Cell 1984; 36: 61–71.

Song, W., Bomsel, M., Casanova, J., Vaerman, J.-P. and Mostov, K. (1994) Stimulation of transcytosis of the polymeric immunoglobulin receptor by dimeric IgA. Proc. Natl. Acad. Sci. USA 91, 163–6.

Stevenson, E. M. and Leaver, J. (1994) Chromatographic separation of the proteins of mouse milk. Int. Dairy J. 4, 205–20.

Sztul E S, Howell K E, Palade G E. Biogenesis of the polymeric IgA receptor in rat hepatocytes. I. Kinetic studies of its intracellular forms. J. Cell Biol. 1985; 100: 1248–54.

Thorpe, G. H. G. and Kricka, L. J. (1986) Enhanced chemiluminescent reactions catalyzed by horseradish peroxidase. Methods Enzymol. 133, 331–53.

Uusi-Oukari, M., Hyttinen, J-M., Korhonen, V-P., Väisti, A., Alhonen, L., Jänne, O. A. and Janne, J. (1997) Bovine $a_{s1}$-casein gene sequences direct high level expression of human granulocyte-macrophage colony-stimulating factor in the milk of transgenic mice. Transgenic Res. 6, 75–84.

What is claimed is:

1. A transgenic, non-human mammalian animal whose genome comprises:
   a stably integrated, recombinant nucleic acid encoding a polymeric immunoglobulin receptor (pIgR) protein operatively linked to a mammary specific promoter;
   wherein a mammary gland of said transgenic, non-human mammalian animal over-expresses said pIgR protein as compared to expression of the pIgR protein in a mammary gland of a wild-type, non-human mammalian animal;
   wherein said pIgR protein transports a polymeric immunoglobulin protein across the basolateral side of a mammary gland's epithelial cell to the apical side of the mammary gland's epithelial cell as compared to a different immunoglobulin protein located on the epithelial cell's basolateral side.

2. The transgenic, non-human mammalian animal of claim 1, wherein the polymeric immunoglobulin protein is selected from the group consisting of IgM and IgA.

3. The transgenic, non-human mammalian animal of claim 1, wherein the immunoglobulin protein located on the epithelial cell's basolateral side is IgG.

4. The transgenic, non-human mammalian animal of claim 1, wherein said transgenic, non-human mammalian animal over-expresses said pIgR protein at least 10-fold higher than the expression of the pIgR protein in the wild-type, non-human mammalian animal.

5. A method of making the transgenic, non-human mammalian animal of claim 1, said method comprising:
   producing a DNA construct comprising a nucleic acid encoding the pIgR protein operably linked to a mammary specific promoter that drives expression of said pIgR protein in a mammary gland epithelial cell;
   introducing said DNA construct into fertilized eggs; and
   implanting the fertilized eggs into a pseudopregnant, female non-human mammalian animal, thereby producing the transgenic, non-human mammalian animal of claim 1.

6. The method according to claim 5, wherein said mammary specific promoter is a casein promoter.

7. A method of collecting an immunoglobulin from the transgenic, non-human mammalian animal of claim 1, comprising:
   providing the transgenic, non-human mammalian animal of claim 1; and
   collecting milk comprising said polymeric immunoglobulin protein from the mammary gland of said transgenic, non-human mammalian animal.

8. The method according to claim 7, further comprising isolating said polymeric immunoglobulin protein from the milk.

9. The method according to claim 7, wherein collecting milk comprising said polymeric immunoglobulin protein comprises collecting milk comprising IgM or IgA.

10. The method according to claim 7, further comprising administering an antigen to said transgenic, non-human mammalian animal prior to collecting the milk from the mammary gland.

* * * * *

UNITED STATES PATENT AND TRADEMARK OFFICE
CERTIFICATE OF CORRECTION

PATENT NO. : 6,924,412 B1
APPLICATION NO. : 09/621593
DATED : August 2, 2005
INVENTOR(S) : Nanda de Groot and Herman Albert de Boer It is certified that error appears in the above-identified patent and that said Letters Patent is hereby corrected as shown below:

item (56) References Cited
OTHER PUBLICATIONS:

| | | |
|---|---|---|
| | COLUMN 1 | change "De Groot et al., Over-extension" to --de Groot et al., Over-expression-- |
| | COLUMN 2 | change "1998, THEMES," to --1998, The American Physiological Society,-- change "expression of variant" to --expression of a variant-- change "milk of transgenic mice using lactoferrin sequence" to --milk of transgenic mice using genomic lactoferrin sequence-- change "Theuer et al., Angiotensin II induced inflammatio" to --Theuer et al., Angiotensin II induced inflammation--. |
| | COLUMN 1, page 2 | change "Kulseth et al., Cloning aned" to --Kulseth et al., Cloning and-- |

In the specification:

| | | |
|---|---|---|
| COLUMN 1, | LINE 45, | change "(colostrun/milk)" to --(colostrum/milk) -- |
| COLUMN 1, | LINE 61, | change "comprises" to --comprise-- |
| COLUMN 3, | LINE 3, | change "line 33646" to --line 3646-- |
| COLUMN 3, | LINE 59, | change "line3644" to --line 3644-- |
| COLUMN 4, | LINE 7, | change "3 dL" to --13 dL-- |
| COLUMN 5, | LINE 52, | change "colostrun" to --colostrum-- |
| COLUMN 6, | LINE 9, | change "lama" to --llama-- |
| COLUMN 8, | LINE 19, | change "dr." to --Dr.-- |
| COLUMN 8, | LINE 25, | change "FIG." to --FIGS.-- |
| COLUMN 8, | LINE 67, | change "1pIgREI" to --c1pIgREI-- |
| COLUMN 9, | LINE 41, | before second occurrence of "minute" insert --1-- |
| COLUMN 9, | LINE 42, | "change "in case integration" to --in case of integration-- |
| COLUMN 9, | LINE 50, | insert --Northern Blot Analysis of the Transgenic Mice-- |
| COLUMN 10, | LINE 35, | change "th se" to --these-- |
| COLUMN 12, | LINE 23, | change "10" to --10.1-- |
| COLUMN 12, | LINE 27, | change "(FIG. 1B, 1C)" to --" to -- (FIGS. 1B, 1C)-- |

UNITED STATES PATENT AND TRADEMARK OFFICE
CERTIFICATE OF CORRECTION

PATENT NO. : 6,924,412 B1
APPLICATION NO. : 09/621593
DATED : August 2, 2005
INVENTOR(S) : Nanda de Groot and Herman Albert de Boer It is certified that error appears in the above-identified patent and that said Letters Patent is hereby corrected as shown below:

In the specification (continued):

| | | |
|---|---|---|
| COLUMN 15, | LINE 17, | change "Eiffert et al, 1991)" to --(Eiffert et al., 1991)-- |
| COLUMN 16, | LINE 8, | change "line 3644.In" to --line 3644. In-- |
| COLUMN 16, | LINE 27, | change "Underreducing" to --Under reducing-- |
| COLUMN 17, | LINE 27, | change "dine 3643)" to --(line 3643)-- |
| COLUMN 19, | LINE 7, | delete "In" |
| COLUMN 19, | LINE 55, | delete "PA" |
| COLUMN 22, | LINE 29, | change "Väisti," to --Västi,-- |

Signed and Sealed this

Twenty-second Day of August, 2006

JON W. DUDAS
*Director of the United States Patent and Trademark Office*